United States Patent
Miyata et al.

(10) Patent No.: US 8,846,412 B2
(45) Date of Patent: Sep. 30, 2014

(54) MULTIPLE SUBSTANCES-RESPONSIVE GEL, METHOD FOR PRODUCING SAME, AND UTILIZATION OF SAME

(75) Inventors: Takashi Miyata, Osaka (JP); Tadashi Uragami, Osaka (JP)

(73) Assignee: Japan Science and Technology Agency, Kawaguchi-Shi, Saitama (JP)

(*) Notice: Subject to any disclaimer, the term of this patent is extended or adjusted under 35 U.S.C. 154(b) by 0 days.

(21) Appl. No.: 14/001,551

(22) PCT Filed: Aug. 30, 2011

(86) PCT No.: PCT/JP2011/069650
§ 371 (c)(1),
(2), (4) Date: Aug. 26, 2013

(87) PCT Pub. No.: WO2012/117588
PCT Pub. Date: Sep. 7, 2012

(65) Prior Publication Data
US 2013/0330842 A1    Dec. 12, 2013

(30) Foreign Application Priority Data

Feb. 28, 2011 (JP) .................. 2011-043017

(51) Int. Cl.
*G01N 33/543* (2006.01)
*G01N 33/545* (2006.01)
*G01N 33/548* (2006.01)
*G01N 33/559* (2006.01)
*G01N 33/53* (2006.01)

(52) U.S. Cl.
CPC .............. *G01N 33/53* (2013.01); *G01N 33/559* (2013.01)
USPC .............................. 436/501; 436/148; 422/69

(58) Field of Classification Search
None
See application file for complete search history.

(56) References Cited

U.S. PATENT DOCUMENTS

| | | | |
|---|---|---|---|
| 5,739,946 A | 4/1998 | Iwanaga et al. | |
| 6,110,684 A | 8/2000 | Kemper et al. | |
| 6,616,946 B1 | 9/2003 | Meier et al. | |
| 8,586,372 B2 * | 11/2013 | Miyata et al. | 436/148 |
| 2002/0164589 A1 | 11/2002 | Taylor | |
| 2004/0146500 A1 | 7/2004 | Miyata et al. | |
| 2005/0209411 A1 | 9/2005 | Nestler et al. | |
| 2007/0156042 A1 | 7/2007 | Unal | |
| 2010/0063771 A1 | 3/2010 | Miyata | 702/156 |
| 2010/0081204 A1 | 4/2010 | Miyata et al. | 436/94 |

FOREIGN PATENT DOCUMENTS

| | | | | |
|---|---|---|---|---|
| CN | 1653094 A | 8/2005 | | |
| EP | 1852454 A1 | 11/2007 | | |
| EP | 1892519 A1 | 2/2008 | | |
| JP | 09-302263 A | 11/1997 | | |
| JP | 2002-239358 A | 8/2002 | | |
| JP | 2003-514650 A | 4/2003 | | |
| JP | 2004-301529 | 10/2004 | ........... | G01N 33/483 |
| JP | 2005-106533 A | 4/2005 | | |
| JP | 2006-137805 A | 6/2006 | | |
| JP | 2006-138656 | 6/2006 | ........... | G01N 33/544 |
| JP | 2006-161027 A | 6/2006 | | |
| JP | 2006-257139 A | 9/2006 | | |
| JP | 2007-046041 A | 2/2007 | | |
| JP | 2007-244374 | 9/2007 | ............... | C12Q 1/68 |
| WO | WO 2006/118077 | 11/2006 | ............. | G01N 21/27 |
| WO | WO 2008/084571 | 7/2008 | ............... | C12Q 1/68 |

OTHER PUBLICATIONS

Kojima, Y., et al. (2010), "Synthesis of stimuli-responsive gels that swell in response to two proteins", *Polymer Preprints*, 59(2): 3879—Full English Translation Provided.

Kojima, Y., et al. (2010), "Structure and responsive behavior of stimuli-responsive hydrogels that recognize a target protein", *Polymer Preprints*, vol. 59(1): 1516—English Abstract Provided.

Miyata, T., et al. (1999), "A reversibly antigen-responsive hydrogel", *Letters to Nature*, 399: 766-769.

Miyata, T., et al. (2006), "Tumor marker-responsive behavior of gels prepared by biomolecular imprinting", *PNAS*, 103(5): 1190-1193.

Miyata, T., et al. (2010), "Synthesis of molecule-responsive gels having cyclodextrin as ligands and their responsive behavior", *Cyclodextrin Symposium*, 27: 58-59—English Abstract Provided.

Morota, M., et al. (2011), "Synthesis of stimuli-responsive gels that recognize multiple proteins simultaneously", *Polymer Preprints*, 60(1): 1880—Full English Translation Provided, May 10, 2011.

Morota, M., et al. (2011), "Synthesis of bioconjugated gels that recognize two proteins simultaneously", *Proceedings of the 40th Biomedical Polymer Symposium, The society of Polymer Science*, 69-70—Full English Translation Provided, Jul. 15, 2011.

(Continued)

*Primary Examiner* — Shafiqul Haq
*Assistant Examiner* — Galina Yakovleva
(74) *Attorney, Agent, or Firm* — Harness, Dickey & Pierce, P.L.C.

(57) ABSTRACT

A multiple-substance-responsive substance is disclosed, which is capable of simultaneously detecting a plurality of detection target substances by a single measurement. By a multiple-substance-responsive gel including: a plurality of kinds of complexes including (i) specifically binding substances, and (ii) binding partners each specifically and reversibly binding to a corresponding one of the specifically binding substances; and a polymer gel to which the plurality of kinds of complexes are immobilized so as to form cross-links, the plurality of kinds of complexes each being formed by binding between (i) a specifically binding substance among the specifically binding substances and (ii) a corresponding binding partner among the binding partners, a plurality of detection target substances can be simultaneously detected by a single measurement.

9 Claims, 6 Drawing Sheets

(56) References Cited

OTHER PUBLICATIONS

Ohkita, Y., et al. (2009), "Synthesis of antigen-responsive hydrogels using temperature-responsive polymer and their behavior", *Polymer Preprints*, 58(1): 1697—English Abstract Provided.
Notification of Reasons for Refusal dated May 29, 2012 issued in Japanese Application No. 2012-511475—with full English translation.
"DNA & Nucleotides Properties", *Nucleotide & Nucleic Acid Properties*, pp. 1 and 2. http://www.geneinfinity.org/sp/sp_dnaprop.html Printed on Dec. 23, 2011.
Chinese Office Action dated Dec. 31, 2010 issued in Chinese Patent Application No. 200880014924X,—with English Translation.
Hayashi, H., et al., (2004) "pH-Sensitive Nanogel Possessing Reactive PEG Tethered Chains on the Surface," *Macromolecules*, 37: 5389-5396.
International Search Report dated Aug. 5, 2008 issued in PCT Patent Application No. PCT/JP2008/058117.
Japanese Notification of Reasons for Refusal dated Dec. 18, 2012 issued in Japanese Patent Application No. 2007-005227—English Translation.
Miyata, T. et al. (2006) "Synthesis of DNA-responsive Gels Having DNA Duplexes as Crosslinking Points and Their DNA-Recognition Behavior," *Polymer Preprints, The Society of Polymer Science*, Japan 55(1):1957.
Miyata, T., et al. (2007) "Structure Control and Response Behavior of Smart Gel Which Responds to Biomolecule," *Papers at 11th Kansai University Symposium on Innovative Science and Technology, The Organization for Research and Development of Innovative Science and Technology*, Kansai University, pp. 157-158.
Miyata, T., et al., (2006) "Controlled Structures and Responsiveness of Stimuli-responsive Gels That Undergo Volume Changes in Response to Biomolecules,"*Polymer Preprints, The Society of Polymer Science*, Japan, 55(2):4516-4517,1S14.
Miyata, T., et al., (2006) "Preparation of Bioconjugated Hydrogels That Respond to Target Biomolecules," *Polymer Preprints, American Chemical Society*, 1-2.
Miyata, T., et al., (2006) "Synthesis of DNA-responsive Gels of Different Swelling and Shrinking Types and Their Response Behavior," *Polymer Preprints, Society of Polymer Science*, Japan, 55(2), pp. 5349-5350.
Miyata, T., et al., (2006), Biomolecule-Responsive Behavior of Smart Gels Having Biomolecular Complexes as Reversible Cross-Links, *AIChE Annual Meeting*, Dec. 14, 2006, pp. 1-4.
Miyata, T., et al., (2007) "Synthesis of Two DNA-responsive Gels That Swell or Shrink in Response to DNA Sequences," *Abstract of Lectures at 18th Research Workshop on Polymer Gels, The Society of Polymer Science*, Japan, pp. 27-28.
Murakami, Y., et al., (2005) "DNA-Responsive Hydrogels That Can Shrink or Swell," *Biomacromolecules*, 6: 2927-2929.
Murakami, Y., et al., (2005), "Hybrid Hydrogels to Which Single-Stranded (ss) DNA Probe is Incorporated Can Recognize Specific ssDNA," *Macromolecules*, 38(5) 1535-1537.
Nayak et al. (2005), "Soft Nanotechnology with Soft Nanoparticles," *Angew. Chem. Int. Ed.*, 44: 7686-7708.
Office Action dated Nov. 1, 2012 issued in U.S. Appl. No. 12/598,904.
Office Action dated Jun. 11, 2012 issued in U.S. Appl. No. 12/598,904.
Office Action dated Nov. 13, 2013 issued in U.S. Appl. No. 12/448,857.
Office Action dated Feb. 25, 2013 issued in U.S. Appl. No. 12/448,857.
Office Action dated Mar. 27, 2013 issued in U.S. Appl. No. 12/598,904.
Office Action dated Dec. 29, 2011 issued in U.S. Appl. No. 12/448,857.
Office Action dated Jun. 29, 2012 issued in U.S. Appl. No. 12/448,857.
Office Action dated Oct. 3, 2012 issued in U.S. Appl. No. 12/448,857.
Office Action dated Aug. 30, 2013 issued in U.S. Appl. No. 12/448,857.
Ohkawa, K., et al., (2006) "Synthesis of DNA—responsive Gels Using Duplex DNAs as Crosslinking Points," *Abstract of Lectures at 17th Research Workshop on Polymer Gels, The Society of Polymer Science*, Japan pp. 39-40.
Stratagene catalog (1988), p. 39 Published by *Stratagene*, 11011 North Torrey Pines Road, La Jolla, CA 92037, USA.
Umeno D., et al. (1998), "Affinity adsorption separation of mutagenic molecules by polyacrylamide hydrogels comprising double-stranded DNA," *Anal. Chim. Acta.*, 365:101-108.

\* cited by examiner

F I G. 8
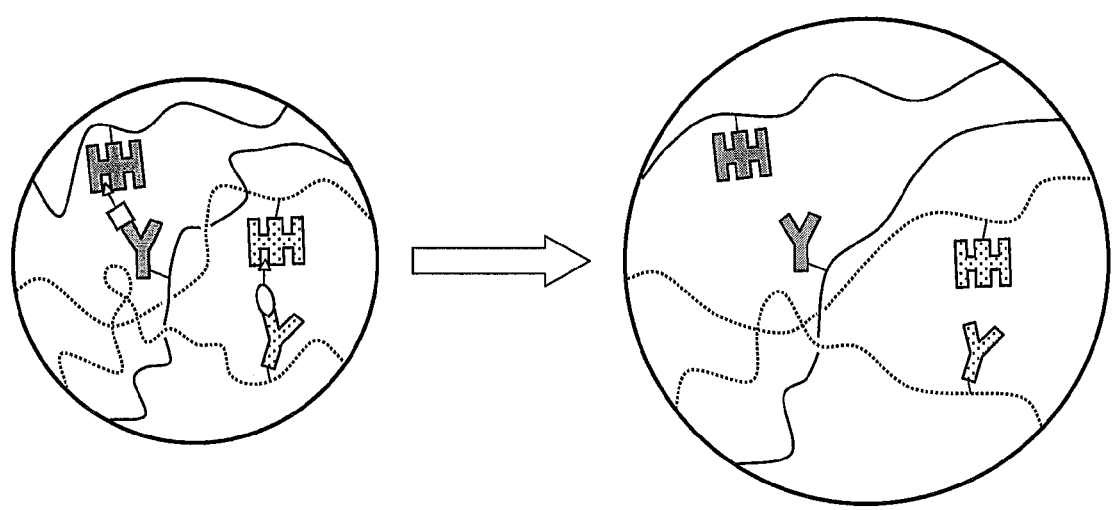

MULTIPLE SUBSTANCES-RESPONSIVE GEL, METHOD FOR PRODUCING SAME, AND UTILIZATION OF SAME

TECHNICAL FIELD

The present invention relates to a multiple-substance-responsive gel, a method for producing the multiple-substances-responsive gel, and use of the multiple-substances-responsive gel, in particular to a multiple-substance-responsive gel that (i) simultaneously recognizes a plurality of detection target substances and (ii) changes in volume as a result of recognizing the plurality of detection target substances, a method for producing the multiple-substances-responsive gel, and use of the multiple-substances-responsive gel.

BACKGROUND ART

In disease markers such as a tumor marker, several kinds of biomolecules are used as marker molecules. Accordingly, if two or more kinds of disease markers for one disease are simultaneously detected, more accurate diagnosis will become possible.

Conventionally, use of an array or microarray of probes each selectively or specifically binding to a detection target substance is known as a method for simultaneously detecting a plurality of biomolecules that are detection target substances. However, according to the method, though a plurality of detection target substances are simultaneously measured, it is required to individually measure the plurality of detection target substances.

The inventors of the present invention have reported a biomolecule responsive gel that (i) senses a target biomolecule and (ii) swells or shrinks as a result of sensing the target biomolecule (for example, see Patent Literature 1 and Non-Patent Literatures 1 and 2). Patent Literature 1 discloses a nucleic-acid-responsive gel that is a gel in which two single-stranded nucleic acids hybridized with each other are introduced as a source of cross-linking points. The gel has a characteristic that when the two single-stranded nucleic acids hybridized with each other come in contact with a target that causes strand exchange and consequent dissociation of the two single-stranded nucleic acids hybridized with each other, the cross-linking points decrease and the gel thereby swells. The gel of Patent Literature 1 is used to detect a target nucleic acid molecule by utilizing such a characteristic. Further, Non-Patent Literature 1 describes that a gel in which an antigen-antibody complex is introduced as a source of cross-linking points gradually swells in the presence of a target antigen. Furthermore, Non-Patent Literature 2 describes that a gel in which a ligand for a target glycoprotein is introduced gradually shrinks in the presence of the target glycoprotein.

CITATION LIST

Patent Literatures

[Patent Literature 1]
Japanese Patent Application Publication, Tokukai, No. 2007-244374 (Publication Date: Sep. 27, 2007)

Non-Patent Literatures

[Non-Patent Literature 1]
Nature 399, 766-769 (1999)
[Non-Patent Literature 2]
Proc. Natl. Acad. Sci. USA, 103, 1190-1193 (2006)

SUMMARY OF INVENTION

Technical Problem

In the aforementioned conventional array or microarray, though a plurality of detection target substances are simultaneously measured, it is required to individually measure the plurality of detection target substances. If it is possible to provide a method for simultaneously detecting such a plurality of detection target substances by a single measurement, it will become possible to simultaneously and simply detect the plurality of detection target substances. However, such a method has not been reported so far.

The present invention is attained in view of the above problem. An object of the present invention is to provide a multiple-substance-responsive substance that is capable of simultaneously detecting a plurality of detection target substances by a single measurement.

Solution to Problem

In order to solve the above problem, a multiple-substance-responsive gel of the present invention includes: a plurality of kinds of complexes including (i) a plurality of kinds of specifically binding substances, and (ii) a plurality of kinds of binding partners each specifically and reversibly binding to a corresponding kind of the plurality of kinds of specifically binding substances; and a polymer gel to which the plurality of kinds of complexes are immobilized so as to form cross-links, the plurality of kinds of complexes each being formed by binding between (i) a specifically binding substance among the plurality of kinds of specifically binding substances and (ii) a corresponding binding partner among the plurality of kinds of binding partners.

The above configuration makes it possible to simultaneously detect a plurality of detection target substances by a single measurement.

Advantageous Effects of Invention

As described above, a multiple-substance-responsive gel of the present invention is arranged to include: a plurality of kinds of complexes including (i) a plurality of kinds of specifically binding substances, and (ii) a plurality of kinds of binding partners each specifically and reversibly binding to a corresponding kind of the plurality of kinds of specifically binding substances; and a polymer gel to which the plurality of kinds of complexes are immobilized so as to form cross-links, the plurality of kinds of complexes each being formed by binding between (i) a specifically binding substance among the plurality of kinds of specifically binding substances and (ii) a corresponding binding partner among the plurality of kinds of binding partners. This makes it possible to detect a plurality of detection target substances by a single measurement.

BRIEF DESCRIPTION OF DRAWINGS

FIG. 8 is a diagram schematically illustrating an embodiment of the multiple-substance-responsive gel.

DESCRIPTION OF EMBODIMENTS

Figure 1:
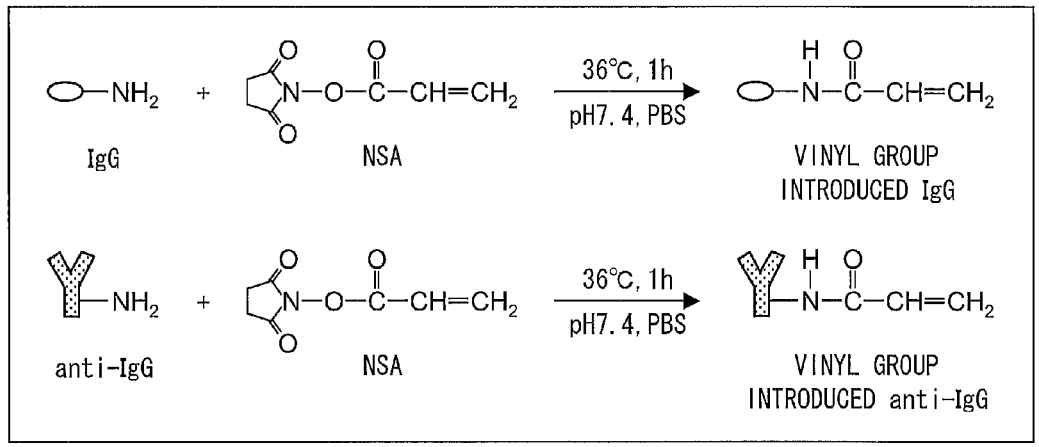
FIG. 1 is a diagram illustrating a process for synthesizing vinyl group introduced IgG and vinyl group introduced anti-IgG in Example 1 of the present invention.

The following discusses in detail embodiments of the present invention. Note, however, that the present invention is by no means limited to these embodiments but encompasses various modifications of these embodiments within the scope described herein.

The inventors of the present invention have previously reported a biomolecule responsive gel in Patent Literature 1, Non-Patent Literature 1, etc. This biomolecule responsive gel utilizes gel swelling caused by a decrease of cross-linking points, which decrease is caused by dissociating a single kind of complex that is introduced in the polymer gel in order to form the cross-linking points. The dissociation of the single kind of complex is carried out by breaking binding of the single kind of complex. In Non-Patent Literature 2, the inventors of the present invention have also reported a gel in which a ligand is introduced. This gel is an imprinted gel. This imprinted gel is obtained by removing a single kind of detection target substance after a complex of two kinds of ligands and the single kind of detection target substance are immobilized so as to form cross-linking points. The two kinds of ligands here each specifically and reversibly bind to the single kind of detection target substance. The gel utilizes gel shrinkage that is caused by formation of cross-linking points owing to binding between a detection target substance and the ligands in the presence of the detection target substance that specifically and reversibly binds to the ligands. In other words, this gel is for detecting an increase or decrease of cross-linking points by a change in volume of the gel. Accordingly, it has been considered that even though an increase or decrease of cross-linking points can be detected by using the gel in which a plurality of kinds of complexes or ligands that bind to a plurality of kinds of detection target substances is introduced, the use of the gel cannot identify which detection target substance causes a change in volume of the gel.

However, the inventors of the present invention immobilized, to a polymer gel, a plurality of kinds of complexes so that these complexes form cross-links, the plurality of kinds of complexes each being formed by binding between a specifically binding substance and a binding partner specifically and reversibly binding to the specifically binding substance. Then, surprisingly, the inventors of the present invention found that whereas (i) a volume of the polymer gel only slightly increases in the presence of a part of the plurality of kinds of detection target substances that dissociate the plurality of kinds of complexes, (ii) the volume of the polymer gel significantly increases in the presence of all the plurality of kinds of detection target substances that dissociate the plurality of kinds of complexes. Further, the inventors of the present invention have arrived at an idea that such a polymer gel allows simultaneous detection of a plurality of kinds of detection target substances only by measurement of a change in volume of the polymer gel, and thereby has accomplished the present invention.

Further, it is expected that a similar phenomenon may occur in the above-described imprinted gel, in a case where ligands that bind to a plurality of kinds of detection target substances are immobilized in place of the ligands that specifically and reversibly bind to a single kind of detection target substance. In other words, a volume of the imprinted gel significantly decreases in a case where all the plurality of kinds of detection target substances are present, as compared to a case where only a part of the plurality of kinds of detection target substances are present. Therefore, the plurality of detection target substances can be simultaneously detected by only a change in volume of such a gel.

(I) Multiple-Substance-Responsive Gel

The multiple-substance-responsive gel of the present invention includes: a plurality of kinds of complexes including (i) a plurality of kinds of specifically binding substances, and (ii) a plurality of kinds of binding partners each specifically and reversibly binding to a corresponding kind of the plurality of kinds of specifically binding substances; and a polymer gel to which the plurality of kinds of complexes are immobilized so as to form cross-links, the plurality of kinds of complexes each being formed by binding between (i) a specifically binding substance among the plurality of kinds of specifically binding substances and (ii) a corresponding binding partner among the plurality of kinds of binding partners.

The "polymer gel" here is not specifically limited as long as the polymer gel is made of a polymer compound which has a network structure and which swells by absorbing liquid. For example, the polymer gel can be a hydrogel made of a polymer compound which has a network structure and which is swelled with water, or alternatively can be an organogel made of a polymer compound which has a network structure and which is swelled with an organic solvent. In particular, the polymer gel is more preferably a hydrogel in view of safety for a case where at least either one of (i) immobilized complexes and (ii) detection target substances are biological substances. Note that: the multiple-substance-responsive gel of the present invention shows a responsive property with respect to detection target substances when the multiple-substance-responsive gel is in a swelled state; however, the "polymer gel" and the multiple-substance-responsive gel in the present invention each encompass a dried gel obtained by removing water, organic solvent, or the like from a swelled gel. Note also that in the present invention, the polymer compound indicates a compound whose molecular weight is 1000 or more. Here in the present specification, the molecular weight is a molecular weight measured by gel permeation chromatography (GPC).

In the present invention, the complexes each may be any complex that is formed by binding of a specifically binding substance and a binding partner that specifically and reversibly binds to the specifically binding substance, which is partnered with that binding partner. Further, each of the specifically binding substance and the binding partner that form a complex is not specifically limited in number. The complex may be formed by one specifically binding substance and one binding partner. Alternatively, the complex may be formed by one specifically binding substance and a plurality of binding partners, or by a plurality of specifically binding substances and one binding partner.

The specifically binding substance and the binding partner each are not specifically limited as long as the specifically binding substance and the binding partner each specifically and reversibly bind to another chemical substance so as to form a complex. However, in a preferred embodiment, at least either one of the specifically binding substance and the binding partner is, for example, a biomolecule. Such a biomolecule encompasses various substances each specifically and reversibly binding to another chemical substance. Preferably, at least either one of the specifically binding substance and the binding partner used in the present invention is such a biomolecule. Such a biomolecule is not specifically limited, but is, for example, protein, nucleic acid, carbohydrate, lipid, glycoprotein, lipoprotein, glycolipid, oligopeptide, polypeptide, a hormone, or a metal ion.

The complex formed by binding of the specifically binding substance and the binding partner encompasses, for example, a complex of an antigen and an antibody, a complex of nucleic acids which hybridize with each other, a complex of an enzyme and a substrate, and a complex of carbohydrate and lectin. Further, the complex may be a complex including a plurality of bindings of at least one kind selected from among a binding of an antigen and an antibody, a binding of nucleic acids which hybridize with each other, a binding of an enzyme and a substrate, and a binding of carbohydrate and lectin. Note here that it does not matter which one of components that form any of these complexes is the specifically binding substance or the binding partner.

In a case where the complex is a complex of nucleic acids that hybridizes with each other, the specifically binding substance is, for example, a single-stranded DNA, a single-stranded RNA, or a single-stranded PNA. The binding partner that specifically and reversibly binds to any of the above-described specifically binding substances is a single-stranded DNA, a single-stranded RNA, a single-stranded PNA or the like that hybridizes with the any of the above-described specifically binding substances. The complex formed by binding between the above specifically binding substance and the above binding partner is made of two single-stranded nucleic acids that are hybridized with each other. These two single-stranded nucleic acids may be two single-stranded DNAs, two single-stranded RNAs, or two single-stranded PNAs, or a combination of two kinds selected from among a single-stranded DNA, a single-stranded RNA, and a single-stranded PNA. At a portion where the two single-stranded nucleic acids are hybridized with each other, the two single-stranded nucleic acids may be fully complementary to each other or alternatively, may have one or more bases mismatching therebetween. Note that the description of Patent Literature 1 is incorporated herein by reference in regard to a type of binding to a polymer gel, a strand exchange, a size of the nucleic acids, etc. in a case where the complex is made of nucleic acids that hybridizes with each other.

When the complex is a complex of an antigen and an antibody or a complex including a binding of an antigen and an antibody, the antigen is not specifically limited. The antigen can be, for example, protein, carbohydrate, lipid, glycoprotein, lipoprotein, glycolipid, oligopeptide, polypeptide, a hormone, or a metal ion. More specifically, such an antigen can be, for example, a tumor marker such as α-fetoprotein (AFP), carcinoembryonic antigen (CEA), CA19-9, basic fetoprotein (BFP), pancreatic oncofetal antigen (POA), aldolase, alkaline phosphatase, γ-glutamyl-transpeptitase, neuron specific enolase, 5'-nucleotide phosphodiesterase isozyme-V (5'-NPD-V), or abnormal prothorombin (PIVKA-II); immune globulin such as IgM, IgG, IgA, IgE, or IgD; a viral antigen such as hepatitis B related-antigen, hepatitis C related-antigen, influenza virus related-antigen, or influenza virus; or a hormone such as a thyroid hormone, or a steroid hormone. Meanwhile, the antibody is not specifically limited as long as the antibody can cause a specific and reversible antigen-antibody reaction with the antigen. The antibody can be either a monoclonal antibody or a polyclonal antibody. Further, the antibody can be Fab, F(ab'), F(ab')$_2$ or the like. In addition, an origin of such an antibody is not specifically limited. The antibody can be prepared by standard methods known in the art. More specifically, the antibody can be obtained, for example, by immunization through administration of an antigen to a mammal such as a rat, a mouse, a rabbit, a horse, a cow, a goat, or a sheep. Alternatively, for example, the antibody can be obtained as a monoclonal antibody that is produced by a hybridoma of a myeloma cell and a B cell that is taken from a spleen of a mouse immunized with an antigen.

In the multiple-substance-responsive gel of the present invention, it is only necessary that a plurality of kinds of complexes be immobilized to a polymer gel, which complexes each are produced by the specifically binding substance and the binding partner that specifically and reversibly binds to the specifically binding substance. A combination of these immobilized complexes is not specifically limited. For example, diagnosis of a disease can be more precisely performed by use of a combination of a plurality of kinds of complexes formed by binding of (i) a plurality of kinds of markers distinct to a certain disease and (ii) binding partners that specifically and reversibly bind to the plurality of kinds of markers, respectively. Alternatively, more than one disease can be simultaneously diagnosed by use of a combination of a plurality of kinds of complexes formed by binding of (i) a plurality of kinds of markers distinct respectively to a plurality of different diseases and (ii) binding partners that specifically and reversibly bind to the plurality of kinds of markers, respectively.

Note that in the present invention, what is meant by "being immobilized to a polymer gel" is to bind to a polymer compound having a network structure that constitutes the polymer gel.

(I-1)

One preferred embodiment of the multiple-substance-responsive gel of the present invention is a multiple-substance-responsive gel in which the complexes are immobilized to the polymer gel so as to from cross-links, by binding of both of the plurality of kinds of specifically binding substances and the plurality of kinds of binding partners to the polymer gel.

Figure 7:
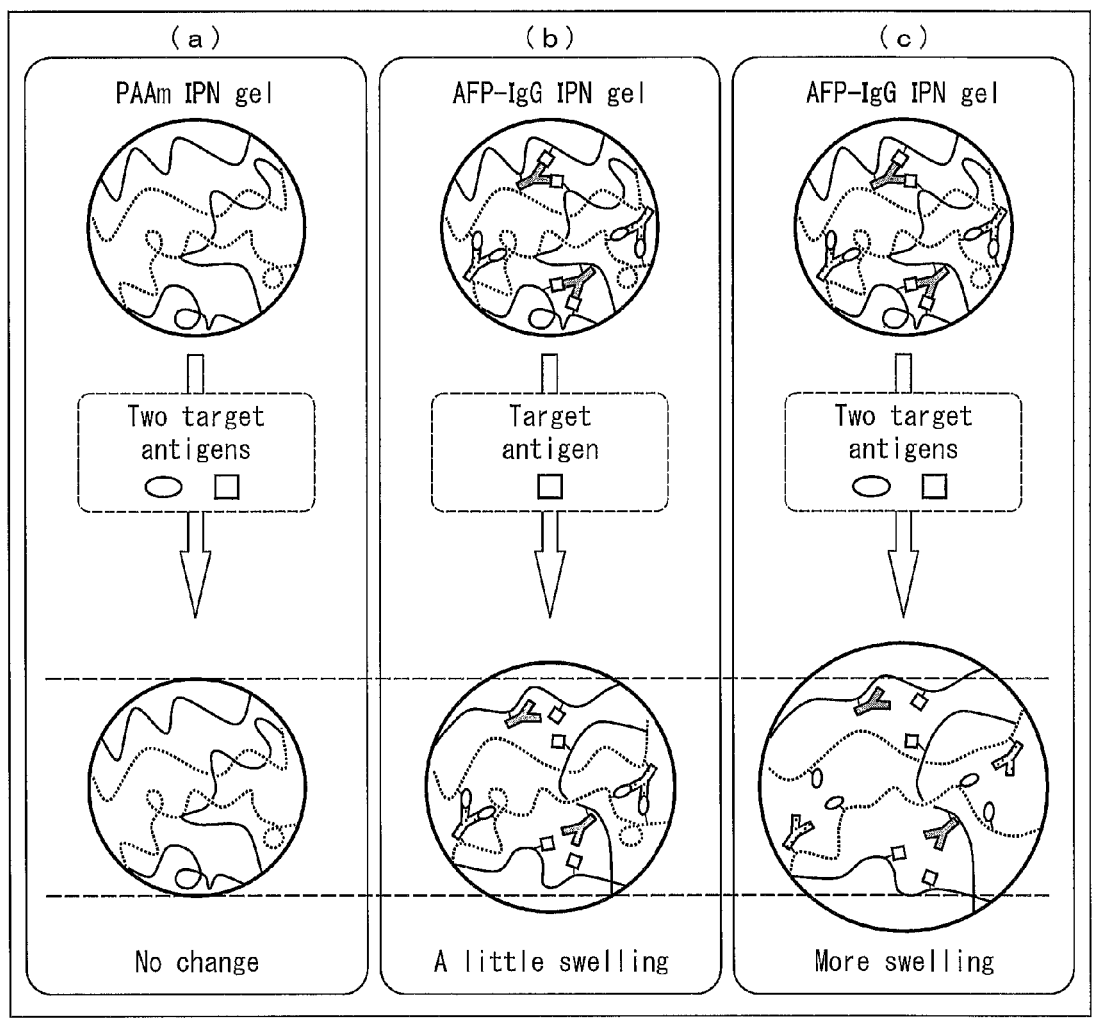
FIG. 7 is a diagram schematically illustrating states in each of which a multiple-substance-responsive gel or a control is brought into contact with a detection target substance(s). (a) of FIG. 7 is a diagram schematically illustrating a state of a control polyacrylamide (PAAm) IPN gel (PAAm IPN gel) in a case where the PAAm IPN gel is brought into contact with a plurality of detection target substances; (b) of FIG. 7 is a diagram schematically illustrating a state of an AFP-IgG antigen-antibody cross-linked IPN gel that is the multiple-substance-responsive gel in a case where the AFP-IgG antigen-antibody cross-linked IPN gel is brought into contact with one of detection target substances; and (c) of FIG. 7 is a diagram schematically illustrating a state of the AFP-IgG antigen-antibody cross-linked IPN gel that is the multiple-substance-responsive gel in a case where the AFP-IgG antigen-antibody cross-linked IPN gel is brought into contact with two detection target substances.

In other words, for example, the complexes are bound to the polymer gel so as to form cross-links, as schematically illustrated in respective upper circles of (b) and (c) of FIG. 7. Note that in respective examples illustrated in (b) and (c) of FIG. 7, first complexes and second complexes are immobilized in the network structure of the polymer gel. The first complexes each are formed by binding between an antigen represented by a rectangle and an antibody that specifically and reversibly binds to the antigen; and the second complexes each are formed by binding between an antigen represented by an oval and an antibody that specifically and reversibly binds to the antigen. Here, each of the cross-links is formed by binding of both of the antigen and the antibody to the network structure of the polymer gel, the antigen and the antibody forming the complex. Here, the antigen is the specifically binding substance (or the binding partner) while the antibody is the binding partner (or the specifically binding substance). In other words, each of the specifically binding substance and the binding partner is bound, at only one side of a cross-link, to the polymer compound that constitutes the network structure of the polymer gel. Formation of a complex results in formation of the cross-link.

Note that in the multiple-substance-responsive gel of the present invention, how the specifically binding substance and the binding partner forming the complex are bound to the polymer gel is not specifically limited. However, preferably, the specifically binding substance and the binding partner are bound to each other, for example, by a chemical bond such as a covalent bond, an ionic bond, or a coordinate bond. This results in stable immobilization of the complex to the polymer gel. Note that the specifically binding substance and the binding partner may be bound to the polymer gel directly or alternatively via a bivalent group.

Here, in the complex, the specifically binding substance and the binding partner bind to each other reversibly. That is, the specifically binding substance and the binding partner bind to each other by a hydrogen bond, a coordinate bond, a covalent bond, an ionic bond, a hydrophobic bond or the like. However, the complex may undergo a reaction that causes dissociation into the specifically binding substance and the binding partner, depending on a change in condition such as temperature or pH, or the presence of other molecules. Such reaction is reversible.

As described above, in the multiple-substance-responsive gel of the present embodiment, the specifically binding substance and the binding partner reversibly bind to each other. Therefore, when there exists (i) a chemical substance that forms more stable complex with either one of the specifically binding substance and the binding partner that form the complex discussed above or (ii) a chemical substance that competitively forms a complex with either one of the specifically binding substance and the binding partner, such a chemical substance replaces the other one of the specifically binding substance and the binding partner that form the complex. Thereby, an exchange of the specifically binding substance or the binding partner occurs.

When the specifically binding substance and the binding partner forming the complex dissociate from each other, the cross-link is broken as in each of respective examples schematically illustrated in respective bottom circles of (b) and (c) of FIG. 7. Accordingly, it is conceivable that cross-linking points decrease. It is well known that in general, a decrease in cross-linking density results in an increase in swelling ratio of a polymer gel. Therefore, as a result of the decrease in cross-linking points, possibly, a swelling ratio of the multiple-substance-responsive gel increases and a volume of the multiple-substance-responsive gel consequently increases. In other words, the multiple-substance-responsive gel of the present embodiment decreases in cross-linking density and thereby increases in volume, when the multiple-substance-responsive gel is brought into contact with such a chemical substance that forms a more stable complex or competitively forms a complex with either one of the specifically binding substance and the binding partner that form the complex discussed above. That is, such a chemical substance that forms a more stable complex or competitively forms a complex with either one of the specifically binding substance and the binding partner that form the complex is a detection target substance for the multiple-substance-responsive gel of the present invention. For example, when the multiple-substance-responsive gel of the present invention is brought into contact with a specifically binding substance or a binding partner, the specifically binding substance or the binding partner can competitively form a complex with one of the specifically binding substance and the binding partner that are immobilized to the polymer gel. Therefore, the multiple-substance-responsive gel of the present invention can detect a substance that is the same as one of the specifically binding substance and the binding partner which are immobilized. Meanwhile, for example, when the multiple-substance-responsive gel of the present invention is brought into contact with a substance that can form a more stable complex with the specifically binding substance or the binding partner, such a substance forms a complex with either one of the specifically binding substance and the binding partner that are immobilized to the polymer gel. Therefore, an exchange of the specifically binding substance or the binding partner with such a substance occurs. This allows the multiple-substance-responsive gel of the present invention to detect a substance that can form a more stable complex with the specifically binding substance or the binding partner.

Here, in the multiple-substance-responsive gel of the present embodiment, the plurality of kinds of complexes including a plurality of kinds of specifically binding substances and a plurality of kinds of binding partners are immobilized to the polymer gel. The plurality of kinds of complexes each are formed by one of the plurality of kinds of specifically binding substances and a corresponding one of the plurality of kinds of binding partners. Accordingly, there are a plurality of kinds of such detection target substances each bindable to a corresponding one of the plurality of kinds of specifically binding substances and the plurality of kinds of binding partners. When a part of the plurality of kinds of detection target substances are present, the multiple-substance-responsive gel slightly increases in volume. The multiple-substance-responsive gel significantly increases in volume only when all the plurality of kinds of detection target substances is present.

In this way, in the multiple-substance-responsive gel of the present embodiment, the plurality of kinds of complexes are formed by respective combinations of the plurality of kinds of specifically binding substances and the plurality of kinds of binding partners, and these plurality of kinds of complexes are immobilized in the network structure of the polymer gel. Thereby, the multiple-substance-responsive gel of the present embodiment increases significantly in swelling ratio only when there exist all the plurality of kinds of detection target substances each bindable to a corresponding one of the plurality of kinds of specifically binding substances and the plurality of kinds of binding partners. Therefore, the plurality of kinds of detection target substances can be simultaneously detected.

In the present embodiment, the polymer gel only needs to contain at least one kind of polymer compound having a network structure. Accordingly, the polymer compound constituting the polymer gel can be made of a single cross-linked polymer or alternatively may be made of an interpenetrating network polymer (IPN (Interpenetrating Polymer Networks) polymer) that is made of a plurality of cross-linked polymers that do not cross-link with each other.

Here, the interpenetrating polymer network is a mixture of a plurality of cross-linked polymers that do not cross-link with each other. These plurality of cross-linked polymers respectively have network structures and form an interpenetrating network structure where the network structures are intricately entangled.

Here, in a case where the polymer gel is made of an interpenetrating polymer network, the complexes are immobilized to the plurality of cross-linked polymers constituting the interpenetrating polymer network, in such a manner that a complex immobilized to one of the plurality of cross-linked polymers is different in kind from another complex immobilized to another one of the plurality of cross-linked polymers. The number of the cross-linked polymers constituting the interpenetrating polymer network is not specifically limited as long as the number is in a range of two or more and ten or less. For example, when the polymer gel is made of an interpenetrating polymer network including a first cross-linked polymer and a second cross-linked polymer, complexes are respectively immobilized to the first cross-linked polymer and the second cross-linked polymer in such a manner that a complex immobilized to the first cross-linked polymer is different in kind from another complex immobilized to the second cross-linked polymer. Note that at this time, the number of kinds of the complexes immobilized to each of the cross-linked polymers may be one or more. However, preferably, a single kind of complex is not immobilized to a plurality of cross-linked polymers. It is expected that in the present embodiment, the above arrangement makes it possible to provide an effect that the swelling ratio significantly increases only when all kinds of cross-links formed by the plurality of kinds of complexes are broken due to dissociation of the plurality of kinds of complexes. The reason for the occurrence of such an effect is unclear. However, it is deduced that such an effect can be obtained because even when only cross-linking points of one kind of cross-linked polymer decrease, the presence of other cross-linked polymer suppresses an increase in volume.

In other words, the following (I) to (III) are deduced. (I) In the interpenetrating polymer network, an IPN structure is formed by interpenetrating networks that do not chemically bind to each other and that are physically entangled with each other. The above discussed complexes are bound, as cross-linking points of each independent network, to the interpenetrating polymer. (II) Such an interpenetrating polymer network has two or more kinds of complexes. Accordingly, even when one kind of detection target substance is present, the interpenetrating polymer network cannot swell because a complex responsive to a different detection target substance does not dissociate. As a result, a level of responsiveness of the interpenetrating polymer network becomes very low. (III) On the other hand, in a case where a plurality of detection target substances are simultaneously present, the complexes respectively corresponding to the plurality of detection target substances dissociate due to an exchange reaction. Therefore, in such a case, the plurality of interpenetrating networks simultaneously expand. As a result, the whole gel can swell.

In a case where the polymer gel is an interpenetrating polymer network, a plurality of cross-linked polymers constituting the interpenetrating polymer network may be identical cross-linked polymers or different cross cross-linked polymers, respectively. However, the plurality of cross-linked polymers are more preferably identical cross-linked polymers. This is because in a case where cross-linked polymers of one kind are combined, phase separation of the plurality of polymers does not occur and therefore, a preferable interpenetrating network structure can be formed. Further, when the plurality of cross-linked polymers are identical to each other, respective changes in volume of the plurality of cross-linked polymers become uniform. This makes a difference between (i) a swelling ratio at the time when all kinds of complexes are dissociated and (ii) a swelling ratio at the time when a part of kinds of complexes are dissociated be constant. Accordingly, a stable detection result can be obtained. Therefore, it is more preferable that the plurality of cross-linked polymers be identical cross-linked polymers.

Further, in a case where the polymer gel is made of a single cross-linked polymer, the plurality of kinds of complexes are immobilized in the single cross-linked polymer. It is conceivable that this provides an effect such that the polymer gel significantly increases in swelling ratio only when all kinds of cross-links formed by the plurality of kinds of complexes are broken due to dissociation of the plurality of kinds of complexes. Such an effect is conceivable for the same reason as in the case where the polymer gel is made of the interpenetrating polymer network.

The cross-linked polymer is not specifically limited, as long as the cross-linked polymer has a network structure and is made of a polymer compound that is swelled with water or an organic solvent. In particular, the polymer gel is preferably made of a polymer compound that is swelled with water. Accordingly, more preferably, the cross-linked polymer is made of a polymer compound obtained by polymerization and cross-linking of hydrophilic monomers. As such monomers, one or a combination of two or more of the following substances can be used, for example: (meth)acrylic acid; alkyl(meth)acrylate; maleic acid; vinyl sulfonic acid; vinyl benzenesulfonic acid; (meth)acrylamide; acrylamide alkylsulfonic acid; (meth)acrylonitrile; amino-substituted (meth) acrylamides such as dimethylaminopropyl(meth)acrylamide; amino-substituted alkyl esters of (meth)acrylic acid such as dimethylaminoethyl(meth)acrylate, diethylaminoethyl (meth)acrylate, and dimethylaminopropyl(meth)acrylate; hydroxyethyl(meth)acrylates such as 2-hydroxyethyl(meth) acrylate; styrene; vinyl pyridine; vinyl carbazole; dimethylamino styrene; alkyl-substituted (meth)acrylamides such as N-isopropyl(meth)acrylamide and N,N'-dimethyl(meth) acrylamide; vinyl acetate; and arylamine. In particular, the above monomers are more preferably selected from among (meth)acrylamide; (meth)acrylic acid; alkyl(meth)acrylate; hydroxyethyl methacrylates such as 2-hydroxyethyl methacrylate; N,N'-dimethyl(meth)acrylamide; N-isopropyl (meth)acrylamide; vinyl acetate; arylamine, and the like. Further, another monomer can be combined as long as the monomer has no adverse effect on performance of a resultant multiple-substance-responsive gel. Note that in the present specification, the expression "(meth)acryl" indicates "acryl" or "methacryl".

Further, more preferably, the cross-linked polymer is obtained by cross-linking through copolymerization or reaction with a cross-linking agent that has two or more reactive functional groups in one molecule. Examples of such reactive functional groups are a vinyl group, a (meth)acryloyl group, a hydroxyl group, a carboxyl group, an amino group, and an isocyanate group. A conventionally-known cross-linking agent can be selected and used as the cross-linking agent. Preferable examples of such a cross-linking agent are a cross-linkable monomer having a polymerizable functional group such as ethylene glycol di(meth)acrylate, propylene glycol di(meth)acrylate, N,N'-methylene bis(meth)acrylamide, tolylene diisocyanate, divinylbenzene, or polyethylene glycol di(meth)acrylate; glutaraldehyde; polyalcohol; polyamine; polycarboxylic acid; and a metal ion. These cross-linking agents can be used solely or in combination of two or more kinds. Alternatively, the cross-linked polymer may be a polymer that is cross-linked only by use of a complex of the present invention by copolymerizing with the complex without use of the cross-linking agent.

Specific examples of the cross-linked polymer are: poly (meth)acrylamide; poly-N-isopropyl(meth)acrylamide; poly-N,N'-dimethyl(meth)acrylamide; poly-2-hydroxyethyl (meth)acrylate; poly(meth)acrylic acid, poly-alkyl(meth) acrylate, polymaleic acid, poly vinyl sulfonic acid, poly vinyl benzenesulfonic acid, poly acrylamide alkylsulfonic acid, poly dimethyl aminopropyl(meth)acrylamide, polyvinyl alcohol, polyethylene glycol, and polypropylene glycol, and a copolymer of any of these substances and (meth)acrylamide, hydroxyethyl(meth)acrylate, (meth)acrylate alkyl ester, or the like; a complex of poly dimethylaminopropyl (meth)acrylamide and polyvinyl alcohol; a complex of polyvinyl alcohol and poly(meth)acrylic acid; metal salt of carboxyalkyl cellulose; poly(meth)acrylonitrile; alginic acid; chitosan; polyallylamine; cellulose, and derivatives, cross-linked substances, and metal salts of the above substances. In particular, the cross-linked polymer is preferably poly(meth)acrylamide, poly(meth)acrylic acid, poly-2-hydroxyethyl (meth)acrylate, poly-alkyl(meth)acrylate, poly-N,N'-dimethyl(meth)acrylamide, poly-N-isopropyl(meth)acrylamide, polyvinyl alcohol, polyarylamine, cellulose, chitosan, alginic acid, or a derivative of any of these substances. Further, the cross-linked polymer preferably has a molecular weight in a range of 1000 or more and 5000000 or less. The molecular weight in the above range is preferable because the cross-linked polymer having such a molecular weight can be easily synthesized by use of a moderate cross-linking agent.

The multiple-substance-responsive gel of the present invention in use for detection of the detection target substances is in a state at equilibrium swelling. When the multiple-substance-responsive gel of the present embodiment comes into contact with the detection target substance, the multiple-substance-responsive gel absorbs liquid and further swells. As a result, the multiple-substance-responsive gel increases in volume. In the present invention, the liquid absorbed at the time of such swelling is not specifically limited, but may be any of water, aqueous buffer solution and organic solvent. Specific examples of such liquid are: water; aqueous buffer solutions such as phosphate buffer solution, Tris buffer solution, and acetate buffer solution; alcohols such as methanol, ethanol, 1-propanol, 2-propanol, 1-butanol, 2-butanol, isobutyl alcohol, and isopentylalcohol; ketones such as acetone, 2-butanone, 3-pentanone, methyl isopropyl ketone, methyl n-propyl ketone, 3-hexanone, and methyl n-butyl ketone; ethers such as diethyl ether, diisopropyl ether, tetrahydrofran, and tetrahydropyran; esters such as acetate ethyl ester; amides such as dimethylformamide and dimethylacetoamide; dimethylsulfoxide; nitriles such as acetonitrile; propylene carbonate; lower saturated hydrocarbons such as pentane, hexane, and cyclohexane; xylene; toluene; and a mixture of two or more kinds of the above substances. In particular, in view of stability in a case where biomolecules are to be detected, the liquid is more preferably water or aqueous buffer solution. When the multiple-substance-responsive gel of the present invention is swelled to equilibrium, a ratio of the liquid contained in the multiple-substance-responsive gel varies depending on a cross-linking density of a polymer gel, a kind of polymer gel or solvent, temperature, pH, ionic strength, and the like. This ratio of the liquid in the multiple-substance-responsive gel at equilibrium swelling is more specifically a ratio with respect to a total weight of the multiple-substance-responsive gel and the liquid contained in the multiple-substance-responsive gel. This ratio is preferably in a range of 30% by weight or more and 99.9% by weight or less, and more preferably, in a range of 70% by weight or more and 99% by weight or less. When the ratio is in the above range, it is possible to obtain a polymer gel having an appropriate strength. Further, the ratio in the above range makes it possible to obtain a polymer network structure in which the detection target substances can be dispersed in the polymer gel. Therefore, the ratio in the above range is preferable.

Further, the cross-linking density of the multiple-substance-responsive gel of the present embodiment is preferably in a range of 0.1 $(mol/m^3)$ or more and 500 $(mol/m^3)$ or less and more preferably, in a range of 1 $(mol/m^3)$ or more and 100 $(mol/m^3)$ or less. When the cross-linking density of the multiple-substance-responsive gel is in the above range, the multiple-substance-responsive gel is expected to show a large change in volume and has a more appropriate strength. Therefore, the cross-linking density in the above range is preferable. Note that in the present specification, the cross-linking density indicates a value obtained by a method described in Examples provided below.

In the multiple-substance-responsive gel of the present embodiment, a total content of the complexes is not specifically limited as long as the total content is in a range that allows the multiple-substance-responsive gel to increase in swelling ratio in response to the detection target substances. The total content of the complexes is preferably in a range of 0.01% by weight or more, more preferably in a range of 0.1% by weight or more, and most preferably in a range of 1% by weight or more, with respect to the multiple-substance-responsive gel in a dried state. The larger the total content of the complexes is, the larger the change in cross-linking density becomes at the time when the multiple-substance-responsive gel responds to the detection target substances. Therefore, the larger total content makes it possible to improve performance of recognition of the detection target substances. There is no specific upper limit for the total content of the complexes, though the performance for of recognition of the detection target substances may not be improved any further from a certain total content of the complexes in a case where too large amount of the complexes are provided.

Further, a form of the multiple-substance-responsive gel of the present invention is not specifically limited, but may be any form. The form may be selected as appropriate depending on an application of the multiple-substance-responsive gel. Examples of the form are cylindrical, plate-like, film-like, particulate, spherical, and rectangular forms. For example, in a case where the multiple-substance-responsive gel is used in a sensor chip or the like, the multiple-substance-responsive gel preferably has a thin-film or film-like form. Meanwhile, when the multiple-substance-responsive gel is used for a diagnosis reagent or the like, the multiple-substance-responsive gel preferably has a particle form or the like.

The multiple-substance-responsive gel of the present invention can be formed into a desired form by using, for example, a method including the steps of first pouring, into a desired mold, a monomer composition and the like that is a material of the multiple-substance-responsive gel before polymerization and then, performing polymerization.

Further, a size of the multiple-substance-responsive gel is not specifically limited, and any preferred size can be selected as appropriate depending on an application. For example, in a case where the multiple-substance-responsive gel is used in a sensor or the like, a small-size polymer gel is preferably used. When the polymer gel is spherical in this case, a diameter of each sphere is preferably in a range of 0.01 μm or more and 100 μm or less. The smaller the size of the multiple-substance-responsive gel becomes, the faster a response speed becomes. Therefore, such a small-size polymer gel can be suitably used for a sensor or the like.

(I-2)

Another preferred embodiment of the multiple-substance-responsive gel of the present invention is an imprinted gel obtained by removing specifically binding substances from the multiple-substance-responsive gel in which each of the plurality of kinds of complexes is formed by binding between (i) one specifically binding substance among the plurality of kinds of specifically binding substances and (ii) a plurality of corresponding binding partners among the plurality of kinds of binding partners, and the plurality of kinds of complexes are immobilized to the polymer gel so as to form cross-links, by binding of the plurality of corresponding binding partners to the polymer gel, the one specifically binding substances not being bound to the polymer gel. Note that in the present invention, the plurality of binding partners bound to the one specifically binding substance together may be referred to as a binding partner set.

The imprinted gel is obtained by removing the one specifically binding substance from the polymer gel, after each of the plurality of kinds of complexes has been immobilized to the polymer gel so as to form a cross-link by binding of (i) the polymer gel and (ii) the plurality of the corresponding binding partners bound to the one specifically binding substance. Accordingly, a binding site complementary to any of the specifically binding substances can be constructed in the imprinted gel. That is, in the polymer gel, the plurality of corresponding binding partners for binding to the one specifically binding substance that has been removed from the polymer gel are provided in such a way to recognize a functional group feature of the one specifically binding substance according to a shape of the one specifically binding substance. A region in the vicinity of thus recognized functional group serves as a site (specifically binding site) for specifically binding to a detection target substance.

In this way, the multiple-substance-responsive gel of the present embodiment is formed by molecular imprinting. The molecular imprinting is a technique for providing a template for a detection target substance in a polymer at the time when the polymer is synthesized. The template is provided in the polymer by (i) first mixing the detection target substance into a monomer for polymer synthesis and carrying out polymerization and (ii) then, removing the detection target substance from thus obtained polymer.

Therefore, the multiple-substance-responsive gel of the present invention encompasses a gel that is an intermediate from which the specifically binding substances are to be removed in production of the imprinted gel. In such a gel, each of the plurality of kinds of complexes is immobilized to the polymer gel so as to form a cross-link by binding of the plurality of binding partners to the polymer gel, the plurality of binding partners being bound to a corresponding one specifically binding substance. In other words, the another preferred embodiment of the multiple-substance-responsive gel of the present invention may be a multiple-substance-responsive gel in which each of the complexes is immobilized to the polymer gel in such a way to form a cross-link, by binding of the plurality of binding partners to the polymer gel, wherein the plurality of binding partners are bound to a corresponding one of the specifically binding substances, but the one specifically binding substances is not bound to the polymer gel.

The gel from which the specifically binding substances are to be removed is an intermediate in production of the imprinted gel. In such a gel, the complexes are bound to the polymer gel so as to form cross-links, as schematically illustrated in a left circle of FIG. 8. Note that in an example illustrated in FIG. 8, a first complex and a second complex are immobilized in a network structure of the polymer gel. The first complex is formed by binding between an antigen represented by a rectangle and two binding partners that specifically and reversibly bind to the antigen. Meanwhile, the second complex is formed by binding between an antigen represented by an oval and two binding partners that specifically and reversibly bind to this antigen. Here, the cross-links are formed by binding of a plurality of binding partners to the polymer gel, wherein the plurality of binding partners each are bound to a corresponding one of the specifically binding substances, and the specifically binding substances are not bound to the polymer gel. In other words, the cross-links are such that each of the plurality of binding partners binds at one side of one of the cross-links to a polymer compound that forms the network structure of the polymer gel, and the cross-links are completed by forming the complexes with the specifically binding substances, respectively.

It is deduced that in the multiple-substance-responsive gel obtained by removing the specifically binding substances from such an intermediate, the cross-links are broken as schematically illustrated in a right circle of FIG. 8 and a decrease in cross-linking points occurs. As a result of this decrease, the multiple-substance-responsive gel increases in swelling ratio.

Note that in the multiple-substance-responsive gel of the present embodiment, a type of binding of the binding partners to the polymer gel is not specifically limited. However, the binding partners are preferably bound to the polymer gel via a chemical bond such as a covalent bond, an ionic bond, or a coordinate bond. This makes it possible to stably immobilize the complexes to the polymer gel. Note that the binding partners may be bound to the polymer gel directly or alternatively via a divalent group. Further, the present embodiment is similar to the embodiment of the above (I-1) in that each of the specifically binding substances and a corresponding one of the binding partners reversibly bind to each other.

Further, in the multiple substance-responsive gel in which the specifically binding substances are removed according to the above-described molecular imprinting, the plurality of binding partners immobilized to the polymer gel recognize detection target substances and bind to the detection target substances when the specifically binding substances are present. As a result, the complexes are formed again.

It is deduced that as a result of re-formation of the complexes, cross-links are also formed again as illustrated in the left circle of FIG. 8 and as a result, cross-linking points increase. It is also conceivable that this increase in cross-linking points results in a decrease in swelling ratio of the multiple-substance-responsive gel and a decrease in volume of the multiple-substance-responsive gel. In other words, the multiple-substance-responsive gel of the present embodiment decreases in volume in the presence of specifically binding substances with which the above complexes are formed. Further, the specifically binding substances with which the complexes are formed are the detection target substances for the multiple-substance-responsive gel of the present invention.

Here, in the multiple-substance-responsive gel of the present embodiment, a plurality of kinds of binding partner sets are immobilized to the polymer gel. The plurality of kinds of binding partner sets are for specifically recognizing the plurality of kinds of specifically binding substances. When there exist a part of the plurality of kinds of detection target substances bindable respectively to the plurality of kinds of binding partner sets, the multiple-substance-responsive gel slightly decreases in volume. Meanwhile, the multiple-substance-responsive gel decreases significantly in volume only when there exist all the plurality of kinds of detection target substances.

In this way, in the multiple-substance-responsive gel of the present embodiment, the plurality of kinds of binding partner sets are immobilized in the network structure of the polymer gel. Accordingly, the multiple-substance-responsive gel significantly decreases in swelling ratio only when there exist all the plurality of kinds of detection target substances bindable respectively to the plurality of kinds of binding partner sets. This makes it possible to simultaneously detect the plurality of detection target substance.

In a case where the polymer gel used in the present embodiment is made of an interpenetrating polymer network, (a) how the plurality of kinds of complexes or the plurality of kinds of binding partners are immobilized and (b) the number of cross-linked polymers are the same as in the embodiment of the above section (I-1).

It is deduced that in the present embodiment, the above feature makes it possible to obtain an effect such that the volume significantly decreases only when all kinds of cross-links respectively formed by the plurality of kinds of complexes are formed. The reason why such an effect can be obtained is not clear. However, it is deduced that such an effect occurs because even when only cross-linking points of one kind of cross-linked polymer increase, the presence of other cross-linked polymer suppresses, as in the case of the above (I-1), the decrease in volume.

Further, when the polymer gel is made of a single cross-linked polymer, an effect similar to that in the case of the above section (I-1) can be obtained. That is, a significant change in volume of the polymer gel can be obtained only when all kinds of cross-links forming the plurality of kinds of complexes are formed.

As to liquid absorbed at the time when the cross-linked polymer or the multiple-substance-responsive gel swells, a ratio of the liquid contained at the time when the multiple-substance-responsive gel is swelled to equilibrium, a cross-linking density of the multiple-substance-responsive gel, a total content of the complexes, and a form and a size of the multiple-substance-responsive gel, the same liquid, ratio, cross-linking density, total content, form and size as in the embodiment of the above section (I-1) apply to the present embodiment.

Note that in the present embodiment, other than the example described above, the one specifically binding substance can be a guest molecule forming a clathrate compound while the plurality of corresponding binding partners can be a plurality of host molecules forming the clathrate compound.

Here, the clathrate compound indicates a compound (i) that is formed by two or more kinds of molecules combined with each other under an appropriate condition and (ii) that has a structure in which a host molecule encloses a guest molecule. Further, the host molecule is not specifically limited as long as the host molecule is a compound capable of including a detection target substance within the host molecule. The host molecule can be any compound capable of forming the clathrate compound as described above. The host molecule can be made of any of, for example, cyclodextrin, a crown compound, cyclophane, azacyclophane, and calixarene and derivatives thereof. These substances have a ring structure, and are capable of recognizing and then including a specific molecule in accordance with a size, a volume, and a shape of a cavity of the ring structure.

(I-3)

As described above, the multiple-substance-responsive gel of one embodiment of the present invention is a polymer gel (i) which slightly changes in volume in response to a part of the plurality of kinds of detection target substances which are exchanged with the plurality of kinds of specifically binding substances or the plurality of kinds of binding partners, the plurality of kinds of binding substances and the plurality of kinds of binding partners in respective combinations constituting the plurality of kinds of complexes immobilized, and (ii) which significantly changes in volume in response to a combination of all the plurality of kinds of detection target substances. More specifically, the multiple-substance-responsive gel is a polymer gel (i) which absorbs liquid and slightly increases in swelling ratio when recognizing a part of the plurality of kinds of detection target substances and (ii) which absorbs liquid and significantly increases in swelling ratio when recognizing a combination of all of the plurality of kinds of detection target substances.

Further, as described above, the multiple-substance-responsive gel of another embodiment of the present invention is a polymer gel to which the plurality of kinds of binding partners specifically recognizing the plurality of kinds of specifically binding substances are immobilized. Further, the multiple-substance-responsive gel slightly decreases in volume when a part of the plurality of kinds of detection target substances are present, which plurality of kinds of detection target substances are bindable respectively to the plurality of kinds of binding partners. Meanwhile, the multiple-substance-responsive gel significantly decreases in volume only when all of the plurality of kinds of detection target substances are present.

In case of disease markers such as a tumor marker, a plurality of kinds of biomolecules are used as marker molecules. Accordingly, more precise diagnosis becomes possible by use of the multiple-substance-responsive gel that changes in volume through simultaneous detection of two or more kinds of disease markers for one disease. Further, it becomes possible to distinguish between (i) a case where only one kind of disease marker is present in regard to marker molecules for a plurality of diseases and (ii) a case where two or more kinds of disease markers are present in regard to the marker molecules. This makes it possible not only to simultaneously diagnose a plurality of diseases but also to widen a range of diagnosis. Therefore, the multiple-substance-responsive gel of the present invention significantly improves preciseness of diagnosis as compared to a conventional technique. Further, the multiple-substance-responsive gel is applicable to a more precise drug-release control system. Further, in the case of a conventional biologically responsive gel, the number of gels required to be synthesized corresponds to the number of target biomolecules. Further, it has been difficult to simultaneously detect a plurality of target biomolecules because each of the gels individually responds to a target molecule. The present invention can solve such problems.

Because the change in volume of the multiple-substance-responsive gel of the present invention is reversible, the multiple-substance-responsive gel can be repeatedly used. Accordingly, the multiple-substance-responsive gel can be further used as a sensor material that is excellent in reproducibility.

An amount of the change in volume is not specifically limited, at the time when the multiple-substance-responsive gel of the present invention changes in volume as a result of recognizing a part of the plurality of kinds of detection target substances. However, it is preferable that an absolute value of the swelling ratio be 1.02 or more. The swelling ratio is a value obtained by dividing a volume after a change in volume by a volume before the change in volume. Further, an amount of the change in volume is not specifically limited at the time when the multiple-substance-responsive gel changes in volume as a result of recognizing all the plurality of kinds of detection target substances. However, in this case, an absolute value of the swelling ratio is preferably 1.02 or more, more preferably 1.08 or more, and most preferably 1.1 or more. The larger the absolute value of the swelling ratio becomes, the better the sensitivity of the multiple-substance-responsive gel becomes. Therefore, a higher absolute value of the swelling ratio is preferable. Further, in regard to the multiple-substance-responsive gel of the present invention, in general, an upper limit of the absolute value of the swelling ratio is approximately 2, though the upper limit varies depending on an amount of cross-links introduced, a kind of the polymer gel or the solvent, a state of a dissociated group in a polymer chain, and the like. Note that in a case where the multiple-substance-responsive gel is in a cylindrical form, the swelling ratio indicates a value obtained by a method described later in Examples. Examples below discuss a method for obtaining a swelling ratio of a cylindrical-form multiple-substance-responsive gel. The method can also be applied to a case where the multiple-substance-responsive gel is, for example, in a spherical form. In such a case where the multiple-substance-responsive gel is in a spherical form, a diameter of a sphere should be used for calculation in place of a "diameter of a cylindrical shape" of Examples.

Further, the multiple-substance-responsive gel of the present invention may be labeled by fine particles such as silica particles, a color material, a molecule having a fluorescent chromophore, a donor or acceptor for utilizing fluorescence resonance energy transfer, or the like. By use of such a multiple-substance-responsive gel, a change in volume of the multiple-substance-responsive gel can be simply detected by use of a spectroscope, a fluorescence microscope, or the like or by visual observation.

(II) Method for Producing Multiple-Substance-Responsive Gel

A method for producing the multiple-substance-responsive gel of the present invention may be any method as long as the method includes a method for producing a multiple-substance-responsive gel including: a plurality of kinds of complexes including (i) a plurality of kinds of specifically binding substances, and (ii) a plurality of kinds of binding partners each specifically and reversibly binding to a corresponding kind of the plurality of kinds of specifically binding substances; and a polymer gel to which the plurality of kinds of complexes are immobilized, the plurality of kinds of complexes each being formed by binding between (i) a specifically binding substance among the plurality of kinds of specifically binding substances and (ii) a corresponding binding partner among the plurality of kinds of binding partners.

(II-1) Case where Multiple-Substance-Responsive Gel is Interpenetrating Polymer Network As one embodiment of the method for producing the multiple-substance-responsive gel of the present invention, a method in a case where the multiple-substance-responsive gel is an interpenetrating polymer network is considered. The method in such a case should include: the first step of producing a first cross-linked polymer in which a first complex is immobilized; and the second step of producing an interpenetrating polymer network made from (i) the first cross-linked polymer in which the first complex is immobilized, the first cross-linked polymer being obtained in the first step and (ii) a second cross-linked polymer in which a second complex is immobilized. Here, the first complex is a complex formed by binding between a first specifically binding substance and a binding partner specifically and reversibly binding to the first specifically binding substance; and the second complex is a complex formed by binding between a second specifically binding substance and another binding partner specifically and reversibly binding to the second specifically binding substance. The first specifically binding substance and the second specifically binding substance are different from each other.

More specifically, the first complex is formed by binding the first specifically binding substance and the binding partner of the first specifically binding substance depending on how the above-described multiple-substance-responsive gel is embodied, after a reactive functional group is introduced into each of the first specifically binding substance and the binding partner of the first specifically binding substance or into only the binding partner depending on how the above-described multiple-substance-responsive gel is embodied. Meanwhile, the second complex is formed by binding the second specifically binding substance and the binding partner of the second specifically binding substance after introduction of a reactive functional group into each of the second specifically binding substance and the binding partner of the second specifically binding substance or into only the binding partner, depending on how the above-described multiple-substance-responsive gel is embodied.

The first step is not specifically limited as long as the first cross-linked polymer in which the first complex is immobilized can be produced in the first step. For example, either one of the following steps (a) and (b) can be suitably employed as the first step:

(a) the first polymerization step of producing a first cross-linked polymer in which a first complex is immobilized, by copolymerizing the first complex with a monomer for forming a first cross-linked polymer, the first complex being formed by a first specifically binding substance and a binding partner that specifically and reversibly binding to the first specifically binding substance, and (b) the step including the complex binding step (b-1) of binding, to a polymer, a first complex being formed by a first specifically binding substance and a binding partner that specifically and reversibly binding to the first specifically binding substance and the first cross-linking step (b-2) of producing a first cross-linked polymer in which the first complex is immobilized, by reacting, with a cross-linking agent, the polymer to which the first complex is bound, which polymer is obtained in the complex binding step (b-1).

In the first polymerization step, the first cross-linked polymer in which the first complex is immobilized is obtained by copolymerizing the first complex with the monomer for forming the first cross-linked polymer in the presence or absence of a cross-linking agent. The monomer used in this first polymerization step is the same as the monomer discussed in the above section (I) and an explanation thereof is omitted here.

Similarly, the cross-linking agent used here is the same as the cross-linking agent discussed in the above section (I) and an explanation thereof is omitted here. Note that the first polymerization step is preferably performed in the presence of the cross-linking agent, but may be performed in the absence of the cross-linking agent. In a case where the first polymerization step is performed in the absence of the cross-linking agent, the multiple substance-responsive gel that can be obtained is a multiple-substance-responsive gel that is cross-linked only by the first complex.

Further, in the first polymerization step, the first complex may be copolymerized with another monomer in addition to the above-described monomer and, if necessary, the cross-linking agent. The another monomer is not specifically limited as long as a the another monomer has no adverse effect on performance of a resultant first cross-linked polymer in which the first complex is immobilized in such copolymerization.

Here, a polymerization method is not specifically limited. As the polymerization method, radical polymerization, ionic polymerization, polycondensation, ring opening polymerization or the like can be suitably used. Further, as a solvent used in the polymerization, for example, water, phosphate buffer solution, Tris buffer solution, acetate buffer solution, methanol, ethanol, or the like can be suitably used.

Moreover, a polymerization initiator is not specifically limited. Examples of the polymerization initiator that can be suitably used are persulfates such as ammonium persulfate and sodium persulfate; hydrogen peroxide; peroxides such as t-butyl hydroperoxide and cumene hydroperoxide, azobisisobutylonitrile, benzoyl peroxide, and 2,2'-azobis(2-amidinopropane)dihydrochloride. Among the above polymerization initiators, in particular, initiators such as persulfates and peroxides exhibit oxidizability and such initiators each can also be used, for example, as a redox initiator together with sodium bisulfite or N,N,N',N'-tetramethylethylenediamine. Alternatively, light, radioactive ray, or the like may be used as the polymerization initiator.

Further, a polymerization temperature is not specifically limited. However, the polymerization temperature is preferably a temperature at which the first complex does not dissociate. In a case where the first complex includes a biomolecule, the polymerization temperature is set to a temperature at which the biomolecule does not denature. In addition, a polymerization time is not specifically limited, but in general, in a range of 4 hours to 48 hours.

A concentration of the monomer, cross-linking agent, or the like in the polymerization is not specifically limited as long as the first cross-linked polymer in which the first complex is immobilized can be obtained at the concentration. Further, a concentration of the polymerization initiator is not specifically limited but may be selected as appropriate.

The first cross-linked polymer in which the first complex is immobilized can be obtained by removing unreacted monomer, cross-linking agent, solvent and the like from a reaction mixture obtained in the first polymerization step.

Note that a method for removing such unreacted monomer, cross-linking agent, solvent and the like is not specifically limited, but can be, for example, a method in which the resultant first cross-linked polymer in which the first complex is immobilized is washed in a substantially neutral buffer solution.

The step (b) employs a method in which the first complex is first bound to a polymer and then the polymer to which the first complex is bound is cross-linked, instead of the method in the first polymerization step of producing the first cross-linked polymer in which the first complex is immobilized by copolymerization of the first complex with the monomer forming the first cross-linked polymer in the presence or absence of the cross-linking agent. Note that the first complex here is bound to a non-cross-linked polymer so as to form a cross-link.

In the complex binding step, the first complex is bound to a polymer. The polymer to which the first complex is bound is not specifically limited, but is, for example, a non-cross-linked polymer. The polymer compound discussed in the above section (I) can be suitably used as such a polymer. Note that the polymer compound is preferably a non-cross-linked polymer, but may be a cross-linked polymer that has a network structure as long as the first complex can be bound to the polymer compound. Further, a method for binding the first complex and the polymer is not specifically limited and a conventionally known method can be suitably used.

In the first cross-linking step, the polymer to which the first complex is bound is reacted with a cross-linking agent so that a network structure is formed. The cross-linking agents described in the above section (I) can be suitably used as the cross-linking agent here. Further, conditions for a cross-linking reaction can be selected as appropriate in accordance with a kind of the polymer compound or the cross-linking agent.

The second step is not specifically limited as long as in the step, it is possible to produce an interpenetrating polymer network made from (i) the second cross-linked polymer in which the second complex is immobilized and (ii) the first cross-linked polymer which is obtained in the first step and in which the first complex is immobilized. For example, either one of the following steps (c) and (d) can be suitably employed as the second step:

(c) the step of producing an interpenetrating polymer network made from the first cross-linked polymer in which the first complex is immobilized and a second cross-linked polymer in which the second complex is immobilized, by copolymerizing, in the presence of the first cross-linked polymer in which the first complex is immobilized, (i) a monomer for forming the second cross-linked polymer with (ii) the second complex formed by binding between a second specifically binding substance and a binding partner specifically and reversibly binding to the second specifically binding substance, and (d) the step of producing an interpenetrating polymer network made from the first cross-linked polymer in which the first complex is immobilized and a second cross-linked polymer in which a second complex is immobilized, the step including the sub-steps of (d-1) first binding, to a polymer, a second complex formed by binding a second specifically binding substance and a binding partner specifically and reversibly binding to the second specifically binding substance, and (d-2) then reacting the polymer to which the second complex is bound with a cross-linking agent in the presence of the first cross-linked polymer in which the first complex is immobilized.

In the step (c), the second cross-linked polymer is formed. For formation of the second cross-linked polymer, a polymerization condition should be selected as appropriate. Such a polymerization condition should not allow formation of a cross-link (i) within the first cross-linked polymer in which the first complex is immobilized and (ii) between the second cross-linked polymer and the first cross-linked polymer in which the first complex is immobilized. The following provides an example of the polymerization condition, though the polymerization condition is not specifically limited to this example. That is, it is possible to employ a polymerization method that is different from a method of the first polymerization method, so that no cross-link is formed to the first cross-linked polymer in which the first complex is immobilized. One example of such a polymerization method is a method including the steps of: (i) first selecting, as the first cross-linked polymer in which the first complex is immobilized, a polymer to which no cross-link is formed by light, radioactive ray, or the like; (ii) immersing this first cross-linked polymer in a solution containing the second complex, a monomer for forming the second cross-linked polymer, and if necessary, a cross-linking agent, and thereby causing the first cross-linked polymer to take in the solution; and (iii) then taking out, from the solution, the first polymer having taken in the second complex and the monomer, and/or the cross-linking agent and carrying out polymerization by use of light, radioactive ray, or the like as an initiator.

As to a monomer, a cross-linking agent, whether or not to use a cross-linking agent, a copolymerization or polymerization method with another monomer, a solvent used in polymerization, a polymerization initiator, a temperature condition, a reaction time, and a concentration of the monomer or the like that can be employed in the step (c), as long as the above polymerization condition is satisfied, those described in the first polymerization step can be used and explanations thereof are omitted here.

Thus obtained multiple-substance-responsive gel can be obtained by removing, from a reaction mixture, unreacted monomer, cross-linking agent, solvent, and the like. Note that a method for removing such unreacted monomer, cross-linking agent, solvent, and the like are the same as that explained in the first polymerization step. Furthermore, though the multiple-substance-responsive gel of the present invention is preferably a hydrogel or an organogel, the multiple-substance-responsive gel can be in a dried state. The multiple-substance-responsive gel of the present invention in a dried state can be obtained, for example, by freeze-drying the multiple-substance-responsive gel that has been washed.

The step (d) employs a method in which the second complex is first bound to a polymer and then the polymer to which the second complex is bound is reacted with a cross-linking agent in the presence of the first cross-linked polymer in which the first complex is immobilized, instead of the method in the step (c) of producing an interpenetrating polymer network made from the first cross-linked polymer in which the first complex is immobilized and a second cross-linked polymer in which the second complex is immobilized, by copolymerizing, in the presence of the first cross-linked polymer in which the first complex is immobilized, the second complex with a monomer for forming the second cross-linked polymer. Note that the second complex here is bound to a non-cross-linked polymer so as to form a cross-link.

In the sub-step (d-1) of binding, the second complex is bound to a polymer. Here, a method for binding the polymer to which the second complex is bound and the polymer to which the first complex is bound is the same as that in the step (b).

Further, as the cross-linking agent used in the step (d), the cross-linking agent described in the above section (I) can be suitably used. A condition for a cross-linking reaction may also be selected as appropriate depending on a kind of a polymer compound, a cross-linking agent, and the like.

A method for producing the multiple-substance-responsive gel of the present embodiment only needs to include at least the first step and the second step. The steps may be any combination of methods employable in the first and second steps, respectively. It is possible to suitably employ any of, for example, a combination of the steps (a) and (c), a combination of the steps (a) and (d), a combination of (b) and (c), and a combination of (b) and (d).

Further, a method for producing the multiple-substance-responsive gel of the present embodiment only needs to include at least the above steps. However, in a case where the multiple-substance-responsive gel is an interpenetrating polymer network that is made from three or more cross-linked polymers, the step of polymerizing a third or subsequent cross-linked polymer should be added. For example, in a case where the multiple-substance-responsive gel is an interpenetrating polymer network made from three cross-linked polymers, this interpenetrating polymer network can be produced by copolymerizing a third complex with a monomer for forming a third cross-linked polymer, in the presence or absence of a cross-linking agent and the interpenetrating polymer network that is formed from the first cross-linked polymer in which the first complex is immobilized and the second cross-linked polymer in which the second complex is immobilized. Thus produced interpenetrating polymer network is formed from the first cross-linked polymer in which the first complex is immobilized, the second cross-linked polymer in which the second complex is immobilized, and the third cross-linked polymer in which the third complex is immobilized. Alternatively, such an interpenetrating polymer network can be formed by a method in which after the third complex is bound to a polymer, the third complex is reacted with a cross-linking agent in the presence of the first cross-linked polymer in which the first complex is immobilized and the second cross-linked polymer in which the second complex is immobilized.

(II-2) In Case where Multiple-Substance-Responsive Gel is Made of Single Cross-Linked Polymer As another embodiment of a method for producing the multiple-substance-responsive gel of the present invention, there is a method in a case where the multiple-substance-responsive gel of the present invention is made of a single cross-linked polymer. In such a case, the multiple-substance-responsive gel of the present invention can be produced by, for example, a production method including the polymerization step of copolymerizing at least the first complex, the second complex, and a monomer for forming the cross-linked polymer, in the presence or absence of a cross-linking agent.

As still another embodiment of the method for producing the multiple-substance-responsive gel of the present invention, there is a method including at least: the complex binding step of binding the first complex and the second complex to a polymer; and the cross-linking step of reacting, with a cross-linking agent, the polymer to which the first and second complexes are bound so that a network structure is formed.

Here, the polymer to which the first complex and the second complex are bound is not specifically limited. For example, any polymer compound that is a non-cross-linked polymer and described in the section (I) can be suitably used. Note that the polymer compound is preferably a non-cross-linked polymer, but may alternatively be a cross-linked polymer that has a network structure as long as the first and second polymer complexes can be bound to this cross-linked polymer.

As to a monomer, a cross-linking agent, whether or not to use a cross-linking agent, a method for copolymerization or polymerization with another monomer, a solvent used in polymerization, a polymerization initiator, a temperature condition, a reaction time, a concentration of the monomer or the like, a method for washing the multiple substance-responsive gel, and the like that can be employed in the present embodiment, those described in the method for producing the multiple-substance responsive gel made of an interpenetrating polymer can be applied and therefore, explanations thereof are omitted here.

A method for producing the multiple-substance-responsive gel of the present embodiment only needs to include at least the above steps. In a case where the multiple-substanceresponsive gel is a gel in which three or more kinds of complexes are immobilized, three or more kinds of complexes should be used in the polymerization step.

(II-3) In Case where Multiple-Substance-Responsive Gel is Multiple-Substance-Responsive Gel of Section (I-1)

The multiple-substance-responsive gel of the above (I-1) is a multiple-substance-responsive gel in which the complexes are immobilized to the polymer gel so as to from cross-links, by binding of both of the plurality of kinds of specifically binding substances and the binding partners to the polymer gel. Such a multiple-substance-responsive gel can be produced by a method described in the above section (II-1) or (II-2) by use of (i) a first complex obtained by binding (a) a first specifically binding substance into which a reactive functional group is introduced and (b) a corresponding binding partner into which a reactive functional group is introduced and (ii) a second complex obtained by binding (a) a second specifically binding substance into which a reactive functional group is introduced and (b) a corresponding binding partner into which a reactive functional group is introduced.

Accordingly, the method for producing the multiple-substance-responsive gel of the section (I-1) may further include: the complex forming step of preparing the first complex by binding the first specifically binding substance into which the reactive functional group is introduced and the binding partner into which the reactive functional group is introduced; and the complex forming step of preparing the second complex by binding the second specifically binding substance into which the reactive functional group is introduced and the binding partner into which the reactive functional group is introduced.

The above complex formation steps each can be carried out, for example, by mixing a solution of a specifically binding substance into which a functional group is introduced and a solution of a binding partner into which a reactive functional group is introduced, under a condition where the specifically binding substance and the binding partner bind to each other.

(II-4) In Case where Multiple-Substance-Responsive Gel is Multiple-Substance-Responsive Gel of (I-2)

The multiple-substance-responsive gel of the above section (I-2) is (i) a multiple-substance-responsive gel in which each of the plurality of kinds of complexes is formed by binding between (i) one specifically binding substance among the plurality of kinds of specifically binding substances and (ii) a plurality of corresponding binding partners among the plurality of kinds of binding partners, and the plurality of kinds of complexes are immobilized to the polymer gel so as to form cross-links, by binding of the plurality of corresponding binding partners to the polymer gel, the one specifically binding substances not being bound to the polymer gel or (ii) an imprinted gel obtained by removing the one specifically binding substance from the multiple-substance-responsive gel.

An intermediate gel from which the specifically binding substances are to be removed can be produced by a method described in the above section (II-1) or (II-2) by use of (i) a first complex obtained by binding (a) a first specifically binding substance into which a reactive functional group is not introduced and (b) a corresponding binding partner into which a reactive functional group is introduced and (ii) a second complex obtained by binding (a) a second specifically binding substance into which a reactive functional group is not introduced and (b) a corresponding binding partner into which a reactive functional group is introduced.

Accordingly, the method for producing the multiple-substance-responsive gel of the section (I-2) may further include: the complex forming step of preparing the first complex by binding the first specifically binding substance and the binding partner into which the reactive functional group is introduced; and the complex forming step of preparing the second complex by binding the second specifically binding substance and the binding partner into which the reactive functional group is introduced.

The above complex formation step each can be carried out, for example, by mixing a solution of a specifically binding substance into which a functional group is introduced and a solution of a binding partner into which a reactive functional group is introduced, under a condition where the specifically binding substance and the binding partner bind to each other. Alternatively, an intermediate gel from which the specifically binding substances are to be removed can be produced by first immobilizing at least one of the binding partners to a polymer and then binding, in the presence of a specifically binding substance, the polymer to another binding partner into which a reactive functional group is introduced. This method can be used in place of a method as described in the above section (II-1) or (II-2), that is, a method including the steps of first forming the complex and then (i) copolymerizing the complex with a monomer for forming the cross-linked polymer or (ii) immobilizing the complex to a polymer and thereafter performing cross-linking. More specifically, for example, the first cross-linked polymer in which the first complex is immobilized and the second cross-linked polymer in which the second complex is immobilized each can be produced according to a method described in Non-Patent Literature 2.

In particular, it is possible to suitably employ a method in which a binding site is formed by (i) first forming a complex of a ligand monomer for a target molecule and the target molecule, (ii) then synthesizing a gel by polymerizing the complex with a monomer, and (iii) subsequently removing a template molecule.

The multiple-substance-responsive gel from which the specifically binding substances have been removed can be produced by removing the first specifically binding substance and the second specifically binding substance from the intermediate obtained by the above-described method.

Therefore, the method for producing the multiple-substance-responsive gel of the above section (I-2) may further include the step of removing the first specifically binding substance and the second specifically binding substance.

The method for removing the first specifically binding substance and the second specifically binding substance from the intermediate is not specifically limited. The method may be any method as long as the specifically binding substances each can be removed by breaking reversible binding between the specifically binding substance and the binding partner in each of the complexes. Such a method for removing the specifically binding substances can be a condition that makes it possible to dissociate the complexes. Examples of such a method are, for example, a method in which the intermediate is washed with a solvent having pH at which dissociation of the complexes occurs and a solvent having a high ionic strength at which dissociation of the complexes occurs, a method in which the intermediate is washed with an appropriate solvent at a temperature at which dissociation of the complexes occurs, and a method in which a template molecule is removed from the intermediate by electrophoresis.

[Other Steps]

Further, the method for producing the multiple-substance-responsive gel of the present invention may include the step of introducing a reactive functional group into at least each of (i) (a) both the first specifically binding substance and the corresponding binding partner or (b) only the binding partner and (ii) (a) both the second specifically binding substance and the corresponding binding partner or (b) only the binding partner.

In the step of introducing the reaction functional group, a reactive functional group is introduced into each of the specifically binding substance and the corresponding binding partner that specifically and reversibly bind to the specifically binding substance. The reactive functional group used here is not specifically limited, but can be any group chemically bindable to a polymer compound that forms a network structure of the polymer gel. Examples of such a reaction functional group are: a vinyl group, a (meth)acryloyl group, a hydroxyl group, a carboxyl group, and an amino group.

Further, a method for introducing the reactive functional group is not specifically limited but a conventionally known method can be used. For example, in a case where a vinyl group is to be introduced, it is possible to take a method in which the specifically binding substance whose end is animated or a binding partner whose end is aminated is reacted with N-succinimidyl acrylate.

As the method for producing the multiple-substance-responsive gel of the present invention, the above-described methods can be suitably used. Therefore, the multiple-substance-responsive gel of the present invention encompasses a multiple-substance-responsive gel obtained by the above methods.

(III) Use of Multiple-Substance-Responsive Gel (III-1) Detection Method by Use of Multiple-Substance-Responsive Gel In the multiple-substance-responsive gel of the present invention, the plurality of kinds of complexes are immobilized to a polymer gel, or alternatively a plurality of kinds of binding partners are immobilized. The plurality of kinds of binding partners here are respectively arranged so as to recognize a plurality of kinds of detection target substances by removing the plurality of kinds of specifically binding substances that are the plurality of kinds of target substances from the plurality of kinds of complexes. When a part of the plurality of kinds of detection target substances are present, the multiple-substance-responsive gel slightly increases in volume. Meanwhile, the multiple-substance-responsive gel significantly increases in volume only when all the plurality of kinds of the detection targets substances are present.

Therefore, the multiple-substance-responsive gel of the present invention can detect a part of the plurality of kinds of detection target substances. Further, the multiple-substance-responsive gel can also be used for simultaneously detecting all the plurality of kinds of detection target substances. Therefore, the present invention encompasses a method for detecting the detection target substances by use of the multiple-substance-responsive gel of the present invention. Note that in the present specification, the detection target substance is a substance in response to which the multiple-substance-responsive gel of the present invention changes in volume.

The method of the present invention for detecting detection target substances only needs to include the steps of: immersing the multiple-substance-responsive gel of the present invention in a sample; and detecting the presence or absence of detection target substances by a change in volume of the multiple-substance-responsive gel.

The detection target substances contained in the sample are (i) chemical substances each of which forms a more stable complex with either one of a specifically binding substance and a corresponding binding partner that together form one of the complex or (ii) chemical substances each of which competitively forms a complex with either one of the specifically binding substance and the corresponding binding partner. In the present embodiment in which the specifically binding substances have been removed, the detection target substances are identical to the specifically binding substances that have been removed. More specifically, the detection target substances each are (i) a chemical substance identical to the specifically binding substance or the corresponding binding partner, (ii) in a case where the detection target substances are nucleic acids, a hybridizable nucleic acid regardless of whether or not the hybridizable nucleic acid is fully complementary, or (iii) in a case where the detection target substances are antigens, an antibody binding to a corresponding one of the antigens. In a preferred embodiment, the detection target substances are, for example, the above-described biomolecules.

Examples of the above sample are: urine, blood, blood serum, blood plasma, saliva, joint fluid, ascites fluid, pleural effusion, spinal fluid, phlegm, and lachrymal fluid.

The method for detecting the presence or absence of the detection target substances on the basis of a change in volume of the multiple-substance-responsive gel is not specifically limited but may be a method for detecting a change in volume of a conventionally known stimuli-responsive gel. The method may be, for example, a method in which a change in volume is observed under a microscope, a method in which a change in gel weight is measured by a scale, a method in which a change in wavelength or strength of a structural color produced when fine particles such as silica particles are provided in advance in the multiple-substance-responsive gel is measured, a method in which a color material is dispersed in the multiple-substance-responsive gel and a resultant optical transmittance is measured, or a method in which molecules each having a fluorescent chromophore is introduced into the multiple-substance-responsive gel and a resultant fluorescence strength is measured.

Further, the presence or absence of the detection target substances can also be detected by a method in which a change in weight of the multiple-substance-responsive gel is detected other than the above method in which a change in volume is detected. As a further alternative, the presence or absence of the detection target substances can be detected by a method in which at least either one of the specifically binding substance and the corresponding binding partner is labeled in advance with a florescent material or the like and then detected by a spectroscope or the like, which specifically binding substance and corresponding binding partner together form a complex immobilized in the network structure. Such a method encompasses, for example, a method utilizing fluorescence resonance energy transfer (FRET).

(III-2) Detection Kit

The present invention related to use of the multiple-substance-responsive gel encompasses not only the above-described method for detecting the detection target substances but also a detection kit for detection by the above method. More specifically, the detection kit of the present invention only needs to include at least the multiple-substance-responsive gel of the present invention.

Moreover, the detection kit may further include any of comparative samples (detection target substance, etc.) serving as a control, various buffers, and the like.

By use of the detection kit, detection by the method of the present invention for detecting detection target substances can be more easily and simply carried out. This makes it possible to apply the present invention to industries such as a clinical examination testing industry and a pharmaceutical industry.

Further, by using the present invention, it is possible to easily detect or identify the detection target substances at a high sensitivity. Therefore, the present invention is also applicable to, for example, treatment, prevention, or diagnosis of various diseases, and analysis in scientific and technical research.

(III-3) Detection Device

In a case where the multiple-substance-responsive gel of the present invention is fixed to a sensor that is capable of detecting a change in volume caused by swelling of a polymer gel, it is possible to produce, with use of such a sensor, a detection device capable of easily and reliably detecting detection target substances.

More specifically, the detection device is, for example, a detection device in which the multiple-substance-responsive gel of the present invention is fixed to a surface of a fine sensor chip that is connected to a measurement device for measuring and displaying an increase in volume caused by an increase in swelling ratio of the multiple-substance-responsive gel. By use of such a detection device, it becomes possible to specifically detect the presence or absence of the detection target substances only by putting a sample in contact with the surface of the chip for detection.

The measurement device to which the sensor chip is connected is not specifically limited. Any conventionally known device can be suitably used. An example of such a device is a film thickness measuring device. In this case, the detection target substances can be detected by detecting, as a change in film thickness, a change in volume of the multiple-substance-responsive gel that responds to the detection target substance in a sample.

Further, the measurement device may be a weight scale. In this case, by measuring a change in weight of the multiple-substance-responsive gel caused by taking in detection target substances, detection of the detection target substances becomes possible. This is because when a sample containing the detection target substance is put in contact with the surface of the chip for detection, the detection target substances are taken into the multiple-substance-responsive gel and thereby a weight of the multiple-substance-responsive gel increases. Meanwhile, a swelling ratio of the multiple-substance-responsive gel changes. This change in volume caused by the change in swelling ratio of the multiple-substance-responsive gel depends on an amount of the detection target substances and a weight of the multiple-substance-responsive gel at the time when the multiple-substance responsive gel takes in the detection target substances. Therefore, such detection of the detection target substances becomes possible.

Further, in a case where the multiple-substance-responsive gel labeled by fine particles such as silica particles, a color material, a molecule having a fluorescent chromophore, or the like as described above is used, the measurement device can be, for example, a spectroscope.

Note that the measurement device to which the sensor chip is connected is not limited to the above-described measurement device for measuring and displaying a change in volume. The sensor chip may be connected to any device that is measuring an amount of other item except volume as long as the measurement device can detect exchange by the detection target substance or binding of the detection target substance. Such a measurement device may be a spectroscope for measuring fluorescence resonance energy transfer, or the like. In this case, the multiple-substance-responsive gel may be a multiple-substance-responsive gel labeled by a donor, an acceptor or the like for utilizing fluorescence resonance energy transfer.

In other words, the present application encompasses the following inventions.

The multiple-substance-responsive gel of the present invention includes: a plurality of kinds of complexes including (i) a plurality of kinds of specifically binding substances, and (ii) a plurality of kinds of binding partners each specifically and reversibly binding to a corresponding kind of the plurality of kinds of specifically binding substances; and a polymer gel to which the plurality of kinds of complexes are immobilized so as to form cross-links, the plurality of kinds of complexes each being formed by binding between (i) a specifically binding substance among the plurality of kinds of specifically binding substances and (ii) a corresponding binding partner among the plurality of kinds of binding partners.

In the above arrangement, a plurality of detection target substances can be simultaneously detected by a single measurement.

The multiple-substance-responsive gel of the present invention may be arranged such that: the plurality of kinds of complexes are immobilized to the polymer gel so as to form the cross-links, by (i) binding of the plurality of kinds of specifically binding substances to the polymer gel and (ii) binding of the plurality of kinds of binding partners to the polymer gel.

In the above arrangement, a plurality of detection target substances can be simultaneously detected by detecting an increase in volume.

The multiple-substance-responsive gel of the present invention may be arranged such that: each of the plurality of kinds of complexes is formed by binding between (i) one specifically binding substance among the plurality of kinds of specifically binding substances and (ii) a plurality of corresponding binding partners among the plurality of kinds of binding partners, and the plurality of kinds of complexes are immobilized to the polymer gel so as to form the cross-links, by binding of the plurality of corresponding binding partners to the polymer gel, the one specifically binding substance not being bound to the polymer gel. In this multiple-substance-responsive gel, the one specifically binding substances may be absent.

In the above arrangement, a plurality of detection target substances can be simultaneously detected by detecting a decrease in volume.

The multiple-substance-responsive gel of the present invention may be arranged such that: the polymer gel is an interpenetrating polymer network made of a plurality of cross-linked polymers cross-linked in such a manner that different cross-linked polymers are not cross-linked with each other; and the complexes are arranged such that a complex immobilized to one of the different cross-linked polymers is different in kind from another complex immobilized to another one of the different cross-linked polymers.

The multiple-substance-responsive gel of the present invention may be arranged such that: the polymer gel is made of a single cross-linked polymer; and the plurality of kinds of complexes are immobilized in the single cross-linked polymer.

In the multiple-substance-responsive gel of the present invention, more preferably, at least either one of the specifically binding substance and the corresponding binding partner is a biomolecule.

In the multiple-substance-responsive gel of the present invention, more preferably, at least either one of the specifically binding substance and the corresponding binding partner is protein, nucleic acid, carbohydrate, lipid, glycoprotein, lipoprotein, glycolipid, oligopeptide, polypeptide, a hormone or a metal ion.

The multiple-substance-responsive gel of the present invention may be arranged such that: the plurality of corresponding binding partners each are a host molecule or host molecules that forms a clathrate compound or form a clathrate compound.

The multiple-substance-responsive gel of the present invention may be arranged such that: the host molecule or host molecules are at least one kind of molecule selected from the group consisting of cyclodextrin, a crown compound, cyclophane, azacyclophane, calixarene and derivatives thereof.

The multiple-substance-responsive gel of the present invention is arranged such that: the multiple-substance-responsive gel changes in volume in the presence of a plurality of detection target substances.

A detection method of the present invention includes the steps of: immersing the multiple-substance-responsive gel in a sample; and detecting the presence or absence of detection target substances by a change in volume of the multiple-substance-responsive gel.

A detection kit of the present invention contains the multiple-substance-responsive gel.

A detection device of the present invention contains the multiple-substance-responsive gel.

A method for producing the multiple-substance-responsive gel of the present invention is a method for producing a multiple-substance-responsive gel including: a plurality of kinds of complexes including (i) a plurality of kinds of specifically binding substances, and (ii) a plurality of kinds of binding partners each specifically and reversibly binding to a corresponding kind of the plurality of kinds of specifically binding substances; and a polymer gel to which the plurality of kinds of complexes are immobilized, the plurality of kinds of complexes each being formed by binding between (i) a specifically binding substance among the plurality of kinds of specifically binding substances and (ii) a corresponding binding partner among the plurality of kinds of binding partners. The method includes: the first step of producing a first cross-linked polymer in which a first complex is immobilized; and the second step of producing an interpenetrating polymer network made from (i) the first cross-linked polymer in which the first complex is immobilized, the first cross-linked polymer being obtained in the first step and (ii) a second cross-linked polymer in which a second complex is immobilized. The first step is either one of the following steps (a) and (b): (a) the first polymerization step of producing a first cross-linked polymer in which a first complex is immobilized, by copolymerizing the first complex with a monomer for forming a first cross-linked polymer, the first complex being formed by a first specifically binding substance and a binding partner that specifically and reversibly binding to the first specifically binding substance, and (b) the step including the complex binding step (b-1) of binding, to a polymer, a first complex being formed by a first specifically binding substance and a binding partner that specifically and reversibly binding to the first specifically binding substance and the first cross-linking step (b-2) of producing a first cross-linked polymer in which the first complex is immobilized, by reacting, with a cross-linking agent, the polymer to which the first complex is bound, which polymer is obtained in the complex binding step (b-1). The second step either one of the following steps (c) and (d): (c) the step of producing an interpenetrating polymer network made from the first cross-linked polymer in which the first complex is immobilized and a second cross-linked polymer in which the second complex is immobilized, by copolymerizing, in the presence of the first cross-linked polymer in which the first complex is immobilized, (i) a monomer for forming the second cross-linked polymer with (ii) the second complex formed by binding between a second specifically binding substance and a binding partner specifically and reversibly binding to the second specifically binding substance, and (d) the step of producing an interpenetrating polymer network made from the first cross-linked polymer in which the first complex is immobilized and a second cross-linked polymer in which a second complex is immobilized, the step including the sub-steps of (d-1) first binding, to a polymer, a second complex formed by binding a second specifically binding substance and a binding partner specifically and reversibly binding to the second specifically binding substance, and (d-2) then reacting the polymer to which the second complex is bound with a cross-linking agent in the presence of the first cross-linked polymer in which the first complex is immobilized. The first specifically binding substance is different from the second specifically binding substance in the above steps.

In the above arrangement, it is possible to produce a multiple-substance-responsive gel capable of simultaneously detecting a plurality of detection target substances by a single measurement.

The method for producing the multiple-substance-responsive gel of the present invention may further include: the complex forming step of preparing the first complex by binding a first specifically binding substance into which a reactive functional group is introduced and a corresponding binding partner into which a reactive functional group is introduced; and the complex forming step of preparing the second complex by binding a second specifically binding substance into which a reactive functional group is introduced and a corresponding binding partner into which the reactive functional group is introduced.

The method for producing the multiple-substance-responsive gel of the present invention may further include: the complex forming step of preparing the first complex by binding the first specifically binding substance and a corresponding binding partner into which a reactive functional group is introduced; and the complex forming step of preparing the second complex by binding the second specifically binding substance and a corresponding binding partner into which a reactive functional group is introduced. The method for producing the multiple-substance-responsive gel of the present invention may further include the step of removing the first specifically binding substance and the second specifically binding substance.

EXAMPLES

The following explains the present invention specifically by providing Examples. However, the present invention is by no means limited by these Examples.

Example 1

Production of Multiple-Substance-Responsive Gel

By using α-fetoprotein (AFP) and immune globulin (IgG) as two kinds of specifically binding substances, a multiple-substance-responsive gel was synthesized. The AFP and IgG are tumor markers each of which is an antigenic protein.

<1-1: Synthesis of Vinyl Group Introduced Rabbit IgG and Vinyl Group Introduced Anti-Rabbit IgG>

As illustrated in FIG. 1, a vinyl group introduced rabbit IgG and a vinyl group introduced anti-rabbit IgG were synthesized in a phosphate buffer solution (PBS) (pH7.4), by reacting each of rabbit IgG and anti-rabbit IgG that was an antibody of the rabbit IgG with N-succinimidyl acrylate (NSA).

More specifically, 125 mg (0.5 μmol) of Rabbit IgG was dissolved into 5 ml of 20 mM phosphate buffer (pH: 7.4). Then, 5 mg (30 μmol) of N-succinimidyl acrylate (2 mg NSA/ml DMSO (dimethylsulfoxide)) was added and reaction was moderately carried out at 36° C. for 1 hour.

Then, gel filtration was carried out so that a vinyl group introduced antigen that was a resultant product was isolated. A column was prepared by filling Sephadex into a glass tube, and an absorbance of a solution obtained by the gel filtration was measured over time by an ultraviolet and visible spectrophotometer (UV-2500PC, manufactured by Shimadzu Corporation). Thereby, the vinyl group introduced antigen and unreacted NSA were isolated from each other. The vinyl group introduced antigen was a high-molecular substance, whereas the unreacted NSA was a low-molecular substance. As to a condition for the gel filtration, measurement was carried out at a wavelength of 270 nm because a characteristic absorption wavelength of the antigen was 280 nm and a characteristic absorption wavelength of the NSA was 260 nm.

Next, the following formula was obtained from a calibration curve prepared by using a native antigen to the vinyl group introduced antigen. The native antigen was used here because the vinyl group introduced antigen had a characteristic absorption wavelength at 280 nm which was the same as that of the native antigen. Then, a concentration of the vinyl group introduced antigen was obtained from the following formula:

$$C(mg/L) = 974.89 \times Abs$$

Similarly, a vinyl group introduced anti-rabbit IgG was synthesized. That is, 30 mg of anti-Rabbit IgG was dissolved into 2 ml of PBS. Then, 0.19 mg of NSA (1 mg NSA/ml DMSO) was added and reaction was moderately carried out at 36° C. for 1 hour.

Subsequently, gel filtration was carried out so that a vinyl group introduced antibody that was a resultant product was isolated. Further, a concentration of the vinyl group introduced antibody was obtained from the following formula that had been obtained by a calibration curve prepared:

$$C(mg/L) = 626.3 \times Abs$$

<1-2: Synthesis of Vinyl Group Introduced AFP and Vinyl Group Introduced Anti-AFP>

Figure 2:
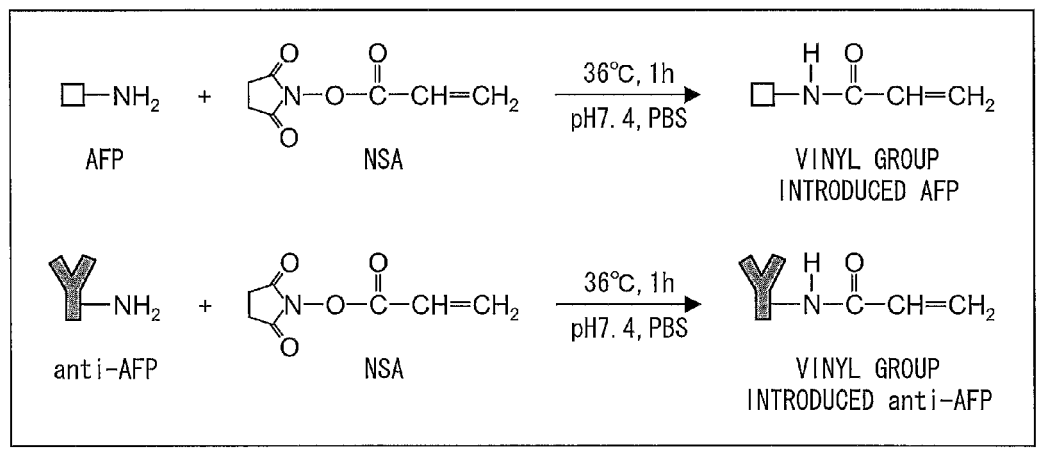
FIG. 2 is a diagram illustrating a process for synthesizing vinyl group introduced AFP and vinyl group introduced anti-AFP in Example 1 of the present invention.

As illustrated in FIG. 2, a vinyl group introduced AFP and a vinyl group introduced anti-AFP were synthesized in a phosphate buffer solution (PBS) (pH7.4), by reacting each of AFP and anti-AFP that was an antibody of the AFP with N-succinimidyl acrylate (NSA).

More specifically, as in the section 1-1 above, 2 mg of AFP was dissolved into 1 ml of PBS. Then, 19.89 μg of NSA (1 mg NSA/ml DMSO; 20 μl) was added and reaction was moderately carried out at 36° C. for one hour. In this case, a molar ratio of AFP:NSA was 1:4.

Then, gel filtration was carried out so that a vinyl group introduced antibody that was a resultant product was isolated. Further, a concentration of the vinyl group introduced AFP was obtained from the following formula that had been obtained from a calibration curve prepared:

$$C(mg/L) = 111.83 \times Abs$$

Further, similarly, 7.46 μg of NSA (1 mg NSA/ml DMSO) was added to 1.5 ml of anti-AFP (Funakoshi Co. Ltd.) and reaction was moderately carried out at 36° C. for 1 hour. Then, a molar ratio of AFP:NSA was 1:2. Note that because an initial concentration of the anti-AFP was unknown, an amount of the anti-AFP was first measured by measurement of an absorbance with use of an ultraviolet and visible spectrophotometer (UV-2550PC, manufactured by Shimadzu Corporation) and then the anti-AFP was used.

Subsequently, gel filtration was carried out so that a vinyl group introduced antibody that was a resultant product was isolated. Further, a concentration of the vinyl group introduced anti-AFP was obtained from the following formula:

$$C(mg/L) = 626.6 \times Abs$$

When the vinyl group introduced antigen and antibody were to be used for gel synthesis, the vinyl group introduced antigen and antibody were condensed (a solution state was maintained) by use of a freeze drier (EYELAFDU-120 Tokyo Rikakiki Co. Ltd.) only in a case where the concentration was low.

<1-3: Preparation of AFP Antigen-Antibody Cross-Linked PAAm Gel (First Cross-Linked Polymer in which First Complex was Immobilized)>

Figure 3:
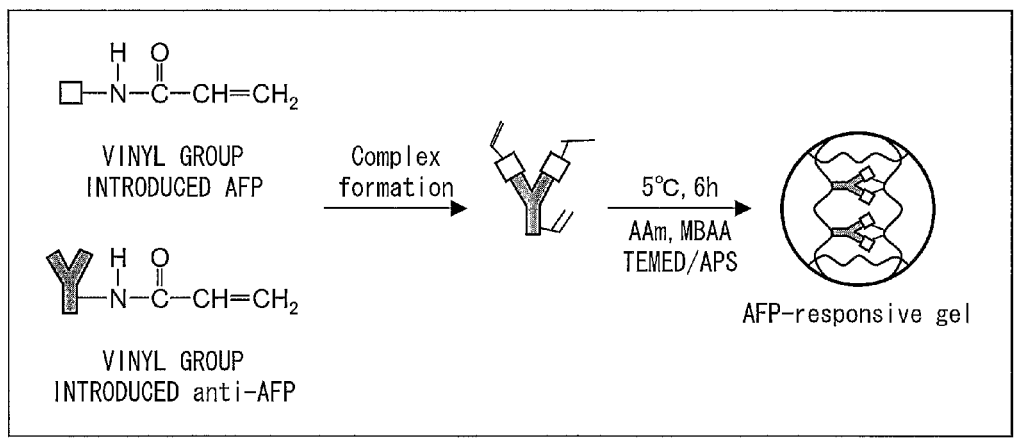
FIG. 3 is a diagram illustrating a process for synthesizing a first cross-linked polymer in which a first complex is immobilized in Example 1 of the present invention.

As illustrated in FIG. 3, by using the vinyl group introduced AFP and the vinyl group introduced anti-AFP that were synthesized in the section 1-2 above, first, an AFP antigen-antibody complex that was a first complex was formed. Then, the AFP antigen-antibody cross-linked gel was synthesized by adding a monomer forming a main chain, a cross-linking agent, and a redox initiator to the AFP antigen-antibody complex and performing copolymerization. Thus synthesized AFP antigen-antibody cross-linked gel was a first cross-linked polymer in which the first complex was immobilized More specifically, 0.2 ml of a PBS solution of the vinyl group introduced AFP containing 0.015 mg of the vinyl group introduced AFP prepared in the above section 1-2 was mixed with 0.2 ml of a PBS solution of the vinyl group introduced anti-AFP containing 0.0075 mg of the vinyl group introduced anti-AFP prepared in the above section 1-2. Thereby, the AFP antigen-antibody complex was formed in advance. Into this solution, the following (a) to (d) were added: (a) 90 mg of acrylamide (AAm) (18 wt % with respect to (AAm+vinyl group introduced antigen solution+vinyl group introduced antibody solution; 500 mg in total)), (b) 0.018 ml of 5 mg/ml PBS solution of N,N'-methylenebisacrylamide (MBAA) (0.1 wt % with respect to AAm), (c) 0.01 ml of 0.8 M PBS solution of N,N,N',N'-tetramethylethylenediamine (0.8 mol PBS solution) (TEMED), and (d) 0.01 ml of 0.1 M PBS solution of ammonium persulfate (APS). Thus obtained solution for polymerization was poured into a glass tube whose inner diameter was 1.5 mm and copolymerization was carried out at 5° C. for 6 hours. Then, a resultant gel obtained in the glass tube was taken out. Subsequently, the resultant gel was sufficiently washed in PBS so that an unreacted substance was removed, and immersed in PBS until equilibrium swelling was reached. Similarly, a polyacrylamide gel was synthesized without an antigen-antibody complex. Whether the gel was washed was checked by measuring a diameter of a cylindrical shape of the gel by use of a microscope. When no change was found in the diameter of the gel in next measurement of the gel after 24 hours, the washing of the gel was ended. In addition, whether the gel was washed was checked by measuring a washed solution by an ultraviolet and visible absorptimeter (UV-2550 manufactured by Shimadzu Corporation).

<1-4: Preparation of AFP-IgG Antigen-Antibody Cross-Linked IPN Gel>

Figure 4:
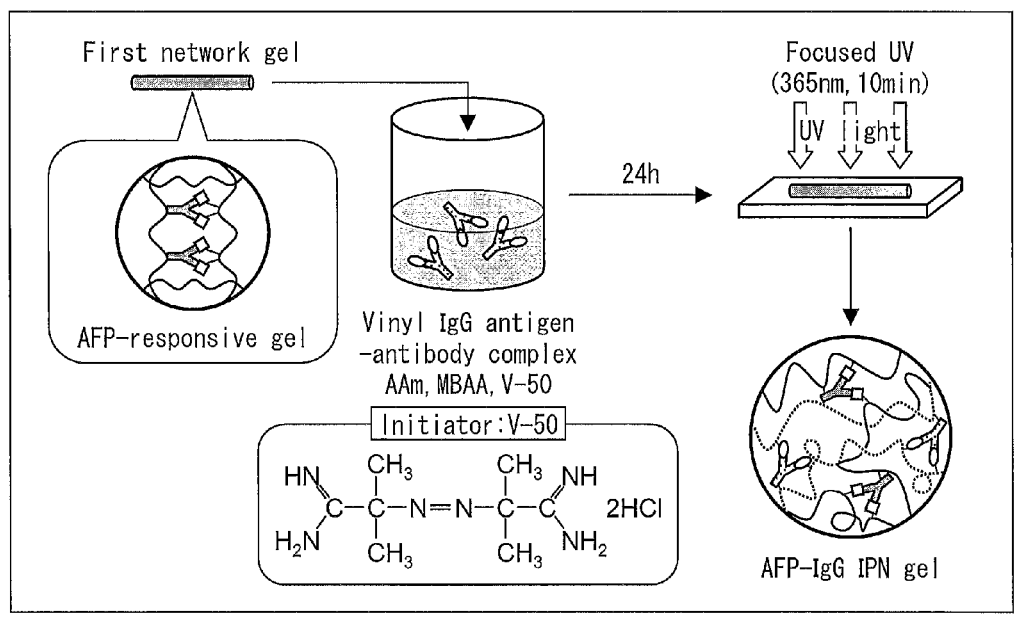
FIG. 4 is a diagram illustrating a process for producing an AFP-IgG antigen-antibody cross-linked IPN gel by first forming a second cross-linked polymer in which a second complex is immobilized, in Example 1 of the present invention.

Further, as illustrated in FIG. 4, thus obtained AFP antigen-antibody cross-linked PAAm gel was immersed into a mixture solution of a vinyl group introduced IgG antigen-antibody complex, AAm, MBAA and a photopolymerization initiator V-50 (manufactured by Wako Pure Chemical Industries, Ltd.). Then, UV light irradiation was carried out so as to form a second cross-linked polymer. In the second cross-linked polymer, the IgG antigen-antibody complex that was a second complex was immobilized. Thereby, the AFP-IgG antigen-antibody cross-linked IPN gel was produced.

More specifically, 0.2 ml of the PBS solution of the vinyl group introduced rabbit IgG containing 4 mg of the vinyl group introduced rabbit IgG prepared in the above section 1-1 was mixed with 0.2 ml of the PBS solution of the vinyl group introduced anti-rabbit IgG containing 2 mg of the vinyl group introduced anti-rabbit IgG prepared in the above section 1-1. Thereby, an antigen-antibody binding was formed in advance. Into thus obtained solution, 90 mg of AAm (ultimate concentration: 18 wt % with respect to (AAm+vinyl group introduced antigen solution+vinyl group introduced antibody solution+PBS solution)) was added and then a total amount of this solution was adjusted with the PBS solution to 500 mg. Subsequently, into a solution into which (a) 0.018 ml of 5 mg/ml PBS solution of MBAA (0.1 wt % with respect to AAm), and (b) 30 μl of 150 mg/ml PBS solution of the photopolymerization initiator V-50 (V-50: 4.5 mg (5 wt % with respect to AAm)) having a structure illustrated in FIG. 4 were dissolved, the AFP antigen-antibody cross-linked PAAm gel prepared in the section 1-3 above was immersed for 24 hours. In this way, the AFP antigen-antibody cross-linked PAAm gel was caused to sufficiently take in monomers and the like. Then, 10-minute irradiation of UV light (365 nm) was carried out onto this AFP antigen-antibody cross-linked PAAm gel by using a handy UV lamp SLUV-6 (manufactured by AS ONE Corporation). As a result, the second cross-linked polymer in which the second complex was immobilized was formed. Thereby, the AFP-IgG antigen-antibody cross-linked IPN gel was synthesized. This AFP-IgG antigen-antibody cross-linked IPN gel was a multiple-substance-responsive gel having an IPN structure.

Comparative Example 1

Production of PAAm IPN Gel

A PAAm IPN gel was prepared under the same condition as in the sections 1-3 and 1-4 of Example 1 except that the vinyl group introduced antigen and the vinyl group introduced antibody were not used.

In other words, to 1 ml of PBS, the following (a) to (d) were added: (a) 90 mg of acrylamide (AAm) (18 wt % with respect to (AAm+PBS)), (b) 0.018 ml of 5 mg/ml PBS solution of N,N'-methylenebisacrylamide (MBAA) (0.1 wt % with respect to AAm), (c) 0.01 ml of 0.8 M PBS solution of N,N,N',N'-tetramethylethylenediamine (TEMED), and (d) 0.01 ml of 0.1 M PBS solution of ammonium persulfate (APS). Then, thus obtained solution for polymerization was poured into a glass tube and copolymerization was carried out so that a first cross-linked polymer gel was synthesized.

Moreover, the first cross-linked polymer gel was first immersed into a solution into which the following (a) to (c) were dissolved: (a) 90 mg of AAm (18 wt % with respect to (AAm+vinyl group introduced antigen solution+vinyl group introduced antibody solution), (b) 0.018 ml of 5 mg/ml PBS solution of MBAA (0.1 wt % with respect to AAm), and (c) 30 μl of 150 mg/ml PBS solution of V-50 (V-50: 4.5 mg (5 wt % with respect to AAm)). Then, by UV light irradiation, a secondary network was formed. Thereby, the IPN gel was produced.

Reference Example 1

Production of AFP Antigen-Antibody Cross-Linked Gel

An AFP antigen-antibody cross-linked gel in which a complex of AFP and an antibody of this AFP was immobilized was synthesized. Here, the AFP antigen-antibody cross-linked PAAm gel (the first cross-linked polymer in which the first complex was immobilized) obtained in the section 1-3 of Example 1 was directly used as the AFP antigen-antibody cross-linked gel.

Reference Example 2

Production of IgG Antigen-Antibody Cross-Linked Gel

A rabbit IgG antigen-antibody cross-linked gel in which a complex of rabbit IgG and an antibody of the rabbit IgG was immobilized was synthesized. Here, the rabbit IgG antigen-antibody cross-linked gel was produced in the same manner as in the section 1-3 of Example 1 except that (a) 0.5 ml of a PBS solution of vinyl group introduced rabbit IgG containing 4 mg of the vinyl group introduced rabbit IgG prepared in the section 1-1 and (b) 0.5 ml of a PBS solution of vinyl group introduced anti-rabbit IgG containing 2 mg of the vinyl group introduced anti-rabbit IgG in the section 1-1 were used in place of (a) 0.2 ml of the PBS solution of vinyl group introduced AFP containing 0.015 mg of the vinyl group introduced AFP and (b) 0.2 ml of the PBS solution of vinyl group introduced anti-AFP containing 0.0075 mg of the vinyl group introduced anti-AFP.

Example 2

Measurement of Swelling Ratio of Multiple-Substance-Responsive Gel

After the AFP-IgG antigen-antibody cross-linked IPN gel produced in Example 1 was swelled to equilibrium in PBS, a swelling ratio was measured for a case where the AFP-IgG antigen-antibody cross-linked IPN gel was immersed in a target antigen aqueous solution. Thereby, a gel response behavior was examined.

First, the AFP-IgG antigen-antibody cross-linked IPN gel washed after having been produced in Example 1 was swelled to equilibrium in PBS. Then, the AFP-IgG antigen-antibody cross-linked IPN gel swelled to equilibrium was cut so as to have a length of approximately 3 to 4 mm. Further, thus cut AFP-IgG antigen-antibody cross-linked IPN gel was immersed at 25° C. into each of an AFP aqueous solution (200 μg/ml) obtained by dissolving AFP into PBS, an IgG solution (2 mg/ml) obtained by dissolving IgG into PBS, and an AFP/IgG mixture solution (AFP: 200 μg/ml, IgG: 2 mg/ml) obtained by dissolving AFP and IgG into PBS. Then, a change in diameter of the AFP-IgG antigen-antibody cross-linked IPN gel that had a cylindrical shape was measured by an optical microscope and a swelling ratio was obtained by the formula provided below. The measurement was carried out by using an inverted research microscope IX 70 (manufactured by OLYMPUS Corporation) and by capturing an image with use of an accessorial digital camera (DP70, manufactured by OLYMPUS). Then, diameters of the gel were measured on a computer and an average value was taken.

$$\text{Swelling Ratio} = (d/d_0)^3 \qquad (1),$$

where: d represents a diameter of the cylindrical shape of the AFP-IgG antigen-antibody cross-linked IPN gel at a given time after immersion of the AFP-IgG antigen-antibody cross-linked IPN gel into the target antigen solution; and do represents a diameter of the cylindrical shape of the AFP-IgG antigen-antibody cross-linked IPN gel at equilibrium swelling (t=0) in PBS.

Further, as a control, a similar measurement was performed by use of the polyacrylamide (PAAm) gel manufactured in Comparative Example 1.

Figure 6:
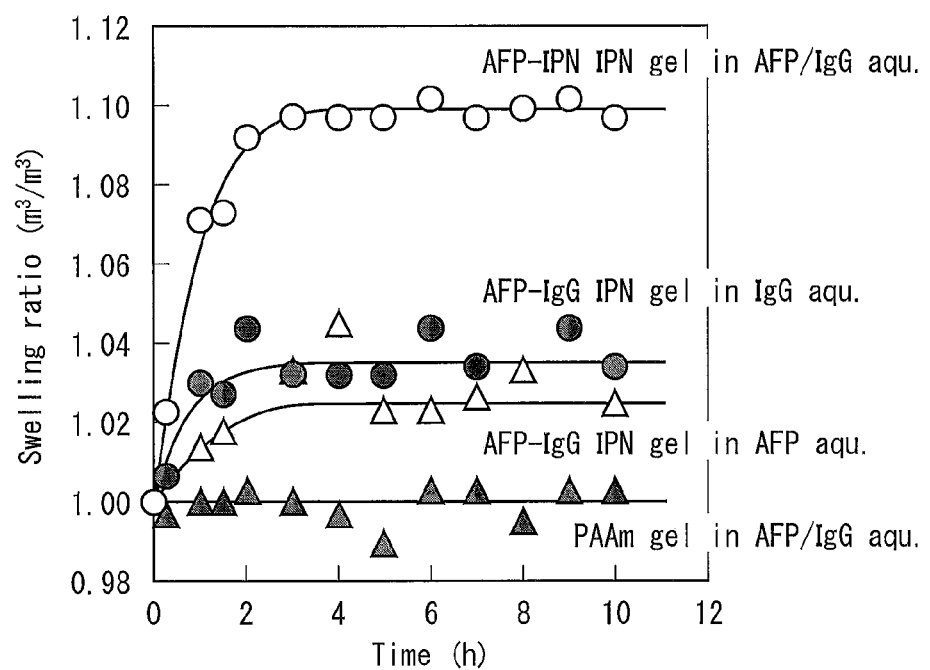
FIG. 6 is a diagram illustrating a result of measuring a swelling ratio in a case where (i) the AFP-IgG antigen-antibody cross-linked IPN gel is swelled to equilibrium in PBS and (ii) then the AFP-IgG antigen-antibody cross-linked IPN gel is immersed in a target antigen (detection target substance) solution, in Example 1 of the present invention.

FIG. 6 shows a result. In FIG. 6, a vertical axis represents a swelling ratio (unit: m$^3$/m$^3$), while a horizontal axis represents a time (unit: hour). In FIG. 6, ○ (open circle) shows a change in swelling ratio in a case where the AFP-IgG antigen-antibody cross-linked IPN gel was immersed in the AFP/IgG mixture solution; • (filled circle) shows a change in swelling ratio in a case where the AFP-IgG antigen-antibody cross-linked IPN gel was immersed in the IgG solution; Δ (open triangle) shows a change in swelling ratio in a case where the AFP-IgG antigen-antibody cross-linked IPN gel was immersed in the AFP solution; and a filled triangle shows a change in swelling ratio in a case where the PAAm gel as a control was immersed in the AFP/IgG mixture solution.

As shown in FIG. 6, the swelling ratio of the AFP-IgG antigen-antibody cross-linked IPN gel increased only very slightly in the AFP solution or IgG solution where only one kind of target antigen was present. However, in the AFP/IgG mixture solution where two kinds of target antigens were simultaneously present, the swelling ratio of the AFP-IgG antigen-antibody cross-linked IPN gel significantly increased. It is clear from this result that the AFP-IgG antigen-antibody cross-linked IPN gel is a multiple-biological-object/multiple-substance-responsive gel whose swelling ratio significantly increases only when two kinds of target antigens are simultaneously detected.

Reference Example 3

Measurement of swelling ratios was carried out for (a) a case where the AFP antigen-antibody cross-linked gel produced in Comparative Example 2 was immersed in PBS where a target antigen of the AFP antigen-antibody cross-linked gel, that is, AFP, was dissolved and (b) a case where the IgG antigen-antibody cross-linked gel produced in Comparative Example 3 was immersed in PBS where a target antigen of the IgG antigen-antibody cross-linked gel, that is, IgG, was dissolved.

Further, similar measurement was carried out by using, as a control, the PAAm gel produced in Comparative Example 1.

Figure 5:
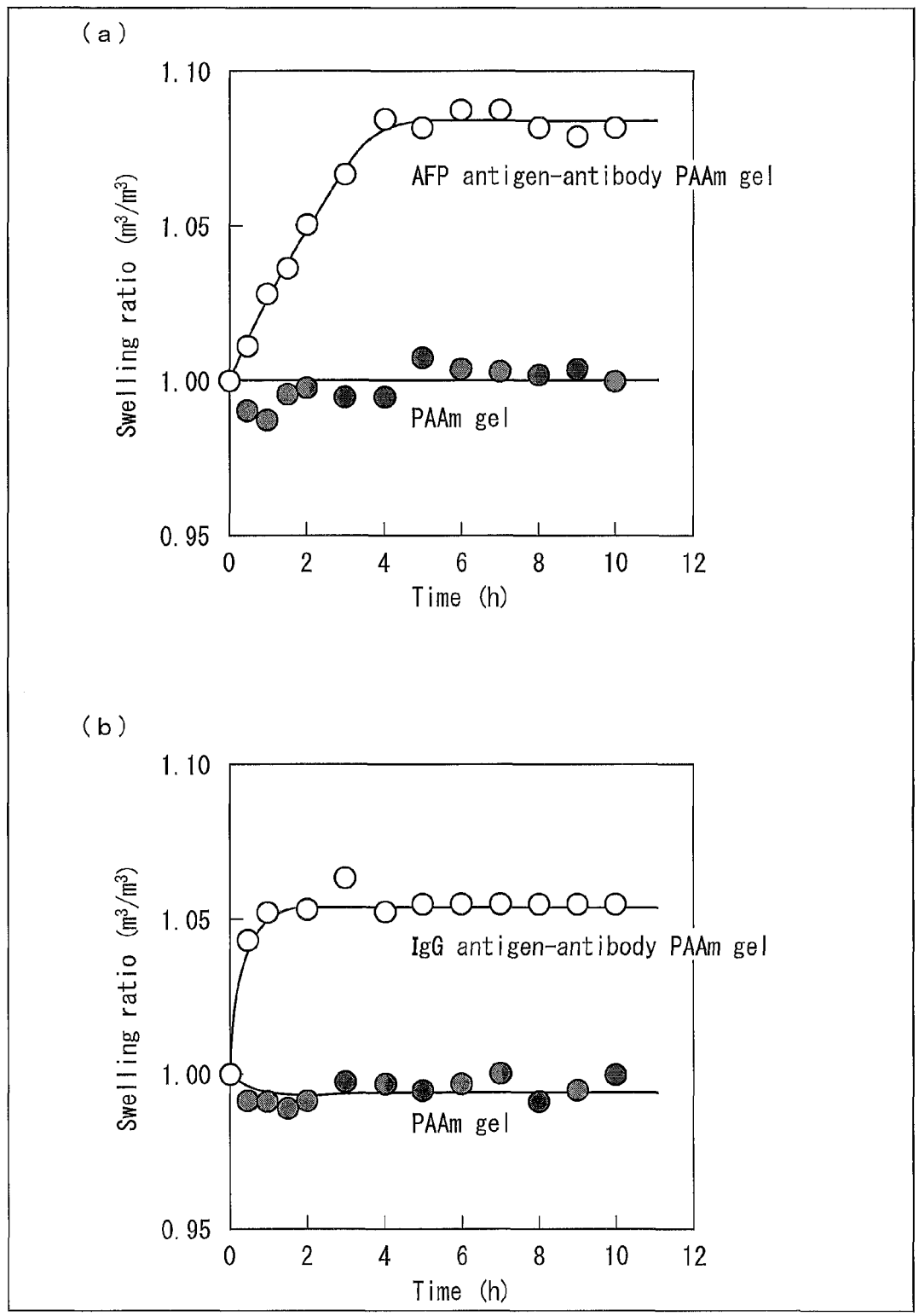
FIG. 5 is a diagram showing results of measuring swelling ratios in respective cases where (a) an AFP antigen-antibody cross-linked gel is immersed in PBS in which AFP that is a target antigen (detection target substance) of the AFP antigen-antibody cross-linked gel is dissolved and (b) IgG antigen-antibody cross-linked gel is immersed in PBS in which IgG that is a target antigen (detection target substance) of the IgG antigen-antibody cross-linked gel is dissolved, in Reference Example 3 of the present invention. (a) of FIG. 5 shows a result of measuring a swelling ratio of the AFP antigen-antibody cross-linked gel; and (b) of FIG. 5 shows a result of measuring a swelling ratio of the IgG antigen-antibody cross-linked gel.

FIG. 5 shows a result of the measurement. In each of (a) and (b) of FIG. 5, a vertical axis represents a swelling ratio (unit: m$^3$/m$^3$) while a horizontal axis represents a time (unit: hour). (a) of FIG. 5 shows a change in swelling ratio in a case where the AFP antigen-antibody cross-linked gel was immersed in PBS where a target antigen of the AFP antigen-antibody cross-linked gel, that is, AFP, was dissolved. ○ (open circle) shows the swelling ratio of the AFP antigen-antibody cross-linked gel; and • (filled circle) shows the swelling ratio of the PAAm gel that is a control. Further, (b) of FIG. 5 shows a change in swelling ratio in a case where the IgG antigen-antibody cross-linked gel was immersed in PBS where a target antigen of the IgG antigen-antibody cross-linked gel, that is, IgG, was dissolved. ○ (open circle) shows the swelling ratio of the IgG antigen-antibody cross-linked gel; and • (filled circle) shows the swelling ratio of the PAAm gel that is a control.

As illustrated in FIG. 5, both the AFP antigen-antibody cross-linked gel and the IgG antigen-antibody cross-linked gel gradually increased in swelling ratio in the presence of respective target antigens, AFP and IgG. Accordingly, it was clarified that each of the AFP antigen-antibody cross-linked gel and the IgG antigen-antibody cross-linked gel exhibits a clear antigen responsive property. It is considered that such an antigen responsive swelling behavior occurs because the presence of a target biomolecule dissociates the antigen-antibody complex that works as a cross-linking point and this dissociation consequently causes a decrease in cross-linking density.

Example 3

Measurement of Cross-Linking Density of Multiple-Substance-Responsive Gel

Next, a response behavior of the AFP-IgG antigen-antibody cross-linked IPN gel in response to two kinds of antigens was studied. For this study, compressive moduli of the AFP-IgG antigen-antibody cross-linked IPN gel in PBS and in the AFP/IgG solution were measured and subsequently, and effective cross-linking densities were calculated.

More specifically, after the AFP-IgG antigen-antibody cross-linked IPN gel was washed, the AFP-IgG antigen-antibody cross-linked IPN gel was swelled to equilibrium in PBS. Regarding the AFP-IgG antigen-antibody cross-linked IPN gel in the state of equilibrium swelling, a diameter and a height were measured by using an optical microscope (NRM-2XZ, manufactured by Carton Optical Industries, Ltd.). Further, by using a compressive modulus apparatus (SMT1-10N, manufactured by Shimadzu Corporation), respective compressive moduli of the AFP-IgG antigen-antibody cross-linked IPN gel in PBS and in the AFP/IgG solution were measured. Then, each effective cross-linking density $v_e$ was calculated for each case by the following formula:

$$G = R \cdot T \cdot v_e \cdot v_2^{1/3},$$

where: G represents a compressive modulus (unit: Pa); R represents a gas constant; T represents an absolute temperature (unit: K), $v_e$ represents an effective cross-linking density (mol/m$^3$); and $v_2$ represents a volume fraction of the polymer compound with respect to a whole swelled gel (polymer compound+solvent). Note that the volume fraction of the polymer compound was approximated so that $W_0/W = V_0/V$ where (W) represents a weight before drying and ($W_0$) represents a weight after drying, after the swelled gel was sufficiently dried in a drier at 50° C. and the weight (W) before drying and the weight ($W_0$) after drying were obtained.

Note that the following shows conditions for the measurement of the compressive modulus:
Mode: load speed 10 mm/min
Jig: compressive
Waveform: sine wave
Limit: load/stress lower limit: 0.000 upper limit: 0.020 N, displacement lower limit: 0.001 upper limit: 50.000 mm Further, regarding the AFP antigen-antibody cross-linked gel, as a control, produced in Reference Example 1, a compressive modulus of this gel in PBS was measured and then an effective cross-linking density was calculated.

Table 1 shows a result of the measurement and calculation. In PBS where no target antigen was present, the effective cross-linking density of the AFP-IgG antigen-antibody cross-linked IPN gel was higher in value than the AFP antigen-antibody cross-linked gel of a primary network. This result shows that the effective cross-linking density increased when an IgG antigen-antibody cross-linked network that was a secondary network was interpenetrated in an AFP antigen-antibody cross-linked network that was a primary network. Further, it is clarified that the cross-linking density of the AFP-IgG antigen-antibody cross-linked IPN gel significantly decreases in a case where this AFP-IgG antigen-antibody cross-linked IPN gel is immersed in the AFP/IgG mixture solution.

TABLE 1

|  | Solution | G (kPa) | $v_e$ (mol/m$^3$) |
|---|---|---|---|
| AFP antigen-antibody cross-linked gel | PBS | 13.6 | 18.1 |
| AFP-IgG antigen-antibody cross-linked IPN gel | PBS | 18.6 | 20.0 |
| AFP-IgG antigen-antibody cross-linked IPN gel | AFP/IgG Mixture Solution | 16.0 | 16.6 |

INDUSTRIAL APPLICABILITY

The multiple-substance-responsive gel of the present invention, for example, can simultaneously detect a plurality of disease markers and thereby makes it possible to precisely diagnose. Further, the multiple-substance-responsive gel of the present invention can be expected to be applied as a novel material that makes it possible to find a disease caused by multiple factors.

Therefore, the present invention is applicable to various chemical industries such as a medicinal chemical manufacturing industry and an industrial chemical manufacturing industry, and further to a medical industry and the like. Furthermore, the present invention is considered to be very useful.

The invention claimed is:

1. A multiple-substance-responsive gel comprising:
    a plurality of kinds of complexes including a plurality of kinds of specifically binding substances, and a plurality of kinds of binding partners each specifically and reversibly binding to a corresponding kind of the plurality of kinds of specifically binding substances; and
    a polymer gel to which the plurality of kinds of complexes are immobilized so as to form cross-links, the plurality of kinds of complexes each being a complex that is formed between one specifically binding substance among the plurality of kinds of specifically binding substances and a corresponding binding partner among the plurality of kinds of binding partners, the complex being immobilized to the polymer gel so as to form the cross-links by binding of both the one specifically binding substance and the corresponding binding partner to the polymer gel.

2. The multiple-substance-responsive gel as set forth in claim 1, wherein:
    the polymer gel is an interpenetrating polymer network made of a plurality of cross-linked polymers cross-linked in such a manner that different cross-linked polymers are not cross-linked with each other; and
    the complexes are arranged such that a complex immobilized to one of the different cross-linked polymers is different in kind from another complex immobilized to another one of the different cross-linked polymers.

3. The multiple-substance-responsive gel as set forth in claim 1 wherein:
    the polymer gel is made of a single cross-linked polymer; and
    the plurality of kinds of complexes are immobilized in the single cross-linked polymer.

4. The multiple-substance-responsive gel as set forth in claim 1, wherein:
    at least either one of the specifically binding substance and the corresponding binding partner is a biomolecule.

5. The multiple-substance-responsive gel as set forth in claim 1, wherein:
    at least either one of the specifically binding substance and the corresponding binding partner is protein, nucleic acid, carbohydrate, lipid, glycoprotein, lipoprotein, glycolipid, oligopeptide, polypeptide, a hormone or a metal ion.

6. The multiple-substance-responsive gel as set forth in claim 1, wherein:
    the multiple-substance-responsive gel changes in volume in the presence of a plurality of detection target substances.

7. A detection method comprising the steps of:
    immersing a multiple-substance-responsive gel as set forth in claim 1 in a sample; and
    detecting the presence or absence of detection target substances by a change in volume of the multiple-substance-responsive gel.

8. A detection kit containing a multiple-substance-responsive gel as set forth in claim 1.

9. A detection device containing a multiple-substance-responsive gel as set forth in claim 1, the multiple-substance-responsive gel being fixed to a surface of a sensor chip that is connected to a measurement device for measuring and displaying an increase in volume caused by an increase in swelling ratio of the multiple-responsive gel.

* * * * *